US007135323B2

(12) United States Patent
Lanahan et al.

(10) Patent No.: US 7,135,323 B2
(45) Date of Patent: Nov. 14, 2006

(54) MICROBIALLY EXPRESSED THERMOTOLERANT PHYTASE FOR ANIMAL FEED

(75) Inventors: Michael L. Lanahan, Morrisville, NC (US); Edward Koepf, Raleigh, NC (US); Keith Kretz, San Marcos, CA (US)

(73) Assignees: Syngenta Participations AG, Basel (CH); Diversa Corporation, San Diego, CA (US)

( * ) Notice: Subject to any disclaimer, the term of this patent is extended or adjusted under 35 U.S.C. 154(b) by 428 days.

(21) Appl. No.: 10/334,672

(22) Filed: Dec. 30, 2002

(65) Prior Publication Data

US 2003/0157646 A1 Aug. 21, 2003

Related U.S. Application Data

(60) Provisional application No. 60/344,523, filed on Dec. 28, 2001.

(51) Int. Cl.
*C12N 9/16* (2006.01)
*C12N 1/20* (2006.01)
*C12N 15/00* (2006.01)
*C07H 21/04* (2006.01)

(52) U.S. Cl. ............... 435/196; 435/252.3; 435/254.2; 435/254.23; 435/320.1; 536/23.2; 536/23.4

(58) Field of Classification Search ................ 435/18, 435/196, 252.3, 254.2, 254.23, 320.1; 536/23.2, 536/23.4
See application file for complete search history.

(56) References Cited

U.S. PATENT DOCUMENTS

| 4,873,192 | A | 10/1989 | Kunkel | 435/91.1 |
|---|---|---|---|---|
| 5,605,793 | A | 2/1997 | Stemmer | 435/6 |
| 5,837,458 | A | 11/1998 | Minshull et al. | 435/6 |
| 6,110,719 | A | 8/2000 | Kretz | 435/196 |
| 6,171,820 | B1 | 1/2001 | Short | 435/69.1 |
| 6,183,740 | B1 | 2/2001 | Short et al. | 424/94.6 |
| 6,238,884 | B1 | 5/2001 | Short et al. | 435/69.1 |
| 6,291,221 | B1 | 9/2001 | van Loon et al. | 435/196 |
| 6,358,709 | B1 | 3/2002 | Short et al. | 435/69.1 |
| 6,451,572 | B1* | 9/2002 | Lei | 435/196 |
| 6,511,699 | B1* | 1/2003 | Lei | 426/630 |
| 6,699,704 | B1 | 3/2004 | van Loon et al. | 435/252.3 |
| 6,720,014 | B1 | 4/2004 | Short et al. | 426/52 |
| 6,855,365 | B1 | 2/2005 | Short et al. | 426/656 |

FOREIGN PATENT DOCUMENTS

| EP | 0 897 985 A | 2/1999 |
|---|---|---|
| WO | WO 00/58481 | 10/2000 |
| WO | WO 01/90333 A2 | 11/2001 |

OTHER PUBLICATIONS

Altschul et al, *Basic Local Alignment Search Tool Journal of Molecular Biology*, vol. 215 (1990) pp. 403-410.

Dassa et al, EBI [online] *Escherichia coli periplasmic phosphoanhydride phosphohydrolase (AppA) gene, complete cds*; retrieved Jan. 14, 2005 from EMBL; accession No. M58708.

Dassa et al, EBI [online] *Periplasmic appA protein precursor*, retrieved Jan. 14, 2005 from GenBank; accession No. P07102.

Dassa J., et al, *The complete nucleotide sequence of the Escherichia coli gene appA reveals significant homology between pH 2.5 acid phosphatase and glucose-1-phosphatase. Journal of Bacteriology*, vol. 172 (1990) pp. 5497-5500.

Lim et al, *Crystal Structures of Escherichia Coli Phytase and its Complex with Phytate Nature Structural Biology*, vol. 11 No. 7 (Jul. 1, 1993) pp. 811-814.

Oh et al, *Catalytic Mechanism and Active Site Residues for a Phytate-Specific Thermostable Phytase from Bacillus Amyloliqufaciens DS11* Abstracts of the General Meeting of the American society for Microbiology, vol. 100, May 22, 2000.

Pen et al, *Phytase-Containing Transgenic Seeds as a Novel Feed Additive for Improved Phosphorus Utilization Bio/Technology*, vol. 11, No. 7 (Jul. 1993) pp. 811-814.

Rodriguez et al, *Site-Directed Mutagenesis Improves Catalytic Efficiency and Thermostability of Escherichia coli pH 2.5 Acid Phosphatase/Phytase Expressed in Pichia pastoris Archives of Biochemistry and Biophysics*, vol. 382, No. 1 (Oct. 1, 2000) pp. 105-112.

Crameri, A. et al. Molecular evolution of an arsenate detoxification pathway by DNA shuffling, Nat. Biotech. 15, 436-438 (May 1997).

Crameri, A. et al. DNA shuffling of a family of genes from diverse species accelerates directed evolution. Nature 391, 288-291 (Jan. 15, 1998).

Dayhoff, M.O., ed. Atlas of Protein Sequence and Structure. vol. 5, Supp. 3, National Biomedical Reserach Foundation, Silver Spring, MD (1979).

Engelen, A.J. et al. Simple and Rapid Determination of Phytase Activity. J. AOAC Int. 77(3), 760-764 (1994).

Engelen, A.J. et al. Determination of Phytase Activity in Feed by a Colorimetric Enzymatic Method: Collaborative Interlaboratory Study. J. AOAC Int. 84(3), 629-633 (2001).

Kornegay, E.T. et al. Response of broilers to graded levels of microbial phytase added to maize-soybean-meal-based diets containing three levels of non-phytate phosphorus. Br. J. Nutr. 75, 839-852 (1996).

(Continued)

Primary Examiner—Tekchand Saidha
(74) Attorney, Agent, or Firm—Mary Kakefuda

(57) ABSTRACT

The invention provides methods for making and using thermotolerant phytases, e.g., a method of using a thermotolerant phytase in feed and food processing and feed or food products comprising a thermotolerant phytase.

18 Claims, 9 Drawing Sheets

OTHER PUBLICATIONS

Kunkel, T,.A. Rapid and efficient site-specific mutagenesis without phenotypic selection. PNAS 82, 488-492 (Jan. 1985).

Kunkel, T.A. et al. Rapid and Efficient Site-Specific Mutagenesis without Phenotypic Selection. Methods in Enzymol. 154, 367-382 (1987).

Moore, J.C. et al. Strategies for the in vitro Evolution of Protein Function: Enzyme Evolution by Random Recombination of Improved Sequences. J. Mol. Biol. 272, 336-347 (1997).

Mroz, Z. et al. Apparent Digestibility and Retention of Nutrients Bound to Phytate Complexes as Influenced by Microbial Phytase and Feeding Regimen Pigs. J. Anim. Sci. 72, 126-132 (1994).

Pallauf, J. and Rimbach, G. Nutritional Significance of Phytic Acid and Phytase. Arch. Anim. Nutr. 50, 301-319 (1997).

Pasamontes, L. et al. Gene Cloning, Purification, and Characterization of a Heat-Stable Phytase from the Fungus Aspergillus fumigatus. Appl. Environ. Microbiol. 63(5), 1696-1700 (May 1997).

Rao, S.V.R. et al. Enhancement of phytate phosphorus availability in the diets of commercial broilers and layers. Animal Feed Sci. Tech. 79, 211-222 (1999).

Rodriguez, E. et al. Different Sensitivity of Recombinant *Aspergillus niger* Phytase (r-PhyA) and *Escherichia coli* pH 2.5 Acid Phosphatase (r-AppA) to Trypsin and Pepsin in Vitro. Arch. Biochem. Biophys. 365(2), 262-267 (May 15, 1999).

Rodriguez, E. et al. Site-Sirected Mutagenesis Improves Catalytic Efficiency and Thermostability of *Escherichia coli* pH 2.5 Acid Phosphatase/Phytase Expressed in *Pichia pastoris*. Arch. Biochem. Biophys. 382(1), 105-112 (Oct. 1, 2000).

Stemmer, W.P.C. Rapid evolution of a protein in vitro by DNA shuffling. Nature 370, 389-391 (Aug. 4, 1994).

Stemmer, W.P.C. DNA shuffling by random fragmentation and reassembly: In vitro recombination for molecular evolution. PNAS 91, 10747-10751 (Oct. 1994).

Walker, J.M. and Gaastra, W. Techniques in Molecular Biology. Croom Helm Ltd, London (1983).

Wyss, M. et al. Biophysical Characterization of Fungal Phytases (myo-inositol Hexakisphosphate Phosphohydrolases): Molecular Size, Glycosylation Pattern, and Engineering of Proteolytic Resistance. Appl. Environ. Microbiol. 65(2), 359-366 (Feb. 1999).

Zhang, J.-H. et al. Directed evolution of a fucosidase from a galactosidase by DNA shuffling and screening. PNAS 94, 4504-4509 (Apr. 1997).

\* cited by examiner

NOV 9X PHYTASE AMINO ACID SEQUENCE
(THE 8 MUTATIONS ARE BOLDED AND UNDERLINED)

(SEQ ID NO:1)

MAQSEPELKLESVVIVSRHGVRAPTKATQLMQDVTPDAWPTWPVKLGELT
PRGGELIAYLGHYWRQRLVADGLLPKCGCPQSGQVAIIADVDERTRKTGEA
FAAGLAPDCAITVHTQADTSSPDPLFNPLKTGVCQLDNANVTDAILERAGG
SIADFTGHYQTAFRELERVLNFPQSNLCLKREKQDESCSLTQALPSELKVSA
DCVSLTGAVSLASMLTEIFLLQQAQGMPEPGWGRITDSHQWNTLLSLHNAQ
FDLLQRTPEVARSRATPLLDLIKTALTPHPPQKQAYGVTLPTSVLFIAGHDTN
LANLGGALELNWTLPGQPDNTPPGGELVFERWRRLSDNSQWIQVSLVFQTL
QQMRDKTPLSLNTPPGEVKLTLAGCEERNAQGMCSLAGFTQIVNEARIPAC
SL

Fig. 1B

GLYCOSYLATION AND GASTRIC STABILITY

| NOV 9X EXPRESSION HOST | GASTRIC STABILITY | THERMAL TOLERANCE* |
|---|---|---|
| E. COLI | 8.4 +/- 1.1 MIN | 10% |
| P. PASTORIS | 10.4 +/- 0.9 MIN | 30% |
| S. POMBE | 29.2 +/- 6.7 MIN | 50% |

*RESIDUAL ACTIVITY FOLLOWING A 5 MIN. HEATING STEP AT 95°C

Fig. 4

MICROBIALLY EXPRESSED THERMOTOLERANT PHYTASE FOR ANIMAL FEED

RELATED APPLICATION

This application claims priority to Application No. 60/344,523, filed Dec. 28, 2001, which is incorporated by reference herein.

FIELD OF THE INVENTION

The present invention generally relates to the field of molecular biology, and more specifically, to the use of a thermotolerant phytase.

BACKGROUND OF THE INVENTION

Phytases (myo-inositol hexakisphosphate phosphohydrolase: EC 3.1.3.8) are enzymes that hydrolyze phytate (myo-inositol hexakisphosphate) to myo-inositol and inorganic phosphate. The enzymes are known to be valuable feed additives. At the close of the twentieth century, annual sales of phytase as an animal feed additive were estimated to exceed $100 million and were growing.

Poultry and pig diets are currently based primarily on cereals, legumes, and oilseed products. About two-thirds of phosphorus (P) present in these feedstuffs occur as phytates, the salts of phytic acid (myo-inositol hexakisphosphate, InsP6) (Jongbloed et al., 1993). Phytate phosphorus in plants is a mixed calcium-magnesium-potassium salt of phytic acid that is present as chelate and its solubility is very low (Pallauf and Rimbach, 1997). Phosphorus in this form is poorly digestible/available for monogastric animals such as human, swine, and poultry.

For the utilization of phytate phosphorus and minerals and trace elements bound in phytic acid complexes, hydrolysis of the ester-type bonded phosphate groups of phytic acid by phytase is necessary (Rimbach et al., 1994). Phytases belong to a special group of phosphatases which are capable of hydrolyzing phytate to a series of lower phosphate esters of myo-inositol and phosphate. Two types of phytases are known: 3-phytase and 6-phytase, indicating the initial attack of the susceptible phosphate ester bond. Although monogastric animals lack sufficient phytase to effectively utilize phytate phosphorous, many fungi, bacteria and yeasts produce phytase that can be used to supplement animal rations.

The beneficial effects of supplementary phytases on phosphorus digestibility and animal performance have been well documented (Mroz et al., 1994; Kornegay et al., 1996; Rao et al., 1999; Ravindran et al., 1999). However, most of these studies have been performed on an ad hoc basis with often only superficial information of the enzymes provided as marketing strategies by the manufacturers. The efficacy of any enzyme preparation depends not only on the type, inclusion rate and level of activity present, but also on the ability of the enzyme to maintain its activity in the different conditions encountered through the gastrointestinal tract and the conditions used for the pre-treatment of a food or feed formulation.

Although numerous phytases are available for use as a supplement, many of the enzymes have certain disadvantages. For example, many of the currently used phytases lose activity during feed pelleting processes due to heat treatment. Additionally, many of the currently used phytases are not adequate in diets containing low levels of supplemental calcium phosphate.

Thus, what is needed is a phytase with improved properties for animal feed and food processing.

SUMMARY OF THE INVENTION

Accordingly, the invention provides methods of preparing and using a nucleic acid molecule (polynucleotide) which encodes a thermotolerant phytase, i.e., a thermotolerant phytase which retains at least 40% activity after 30 minutes at about 60° C., and which has a high specific activity, i.e., at least about 200 U/mg at 37° C. and at acid pH, e.g., pH 4.5. In one embodiment, the invention provides a method to prepare a thermotolerant phytase. The method comprises expressing in a microbial host cell an expression cassette comprising a promoter operably linked to a nucleic acid molecule encoding a thermotolerant phytase which retains at least 40% activity after 30 minutes at 60° C. and has a specific activity of greater than 200 U/mg at pH 4.5 and 37° C. The microbial host cell may be a prokaryotic cell, such as a bacterial cell (e.g., *Escherichia*, *Pseudomonas*, *Lactobacillus*, and *Bacillus*), yeast (e.g., *Saccharomyces*, *Schizosaccharomyces*, *Pichia* or *Hansuela*) or fungal (e.g., *Aspergillus* or *Trichoderma*) cell. In one preferred embodiment, the microbial cell which is employed to prepare the recombinant thermotolerant phytase yields a glycosylated form of the recombinant thermotolerant phytase.

It is preferred that the polynucleotide that encodes the thermotolerant phytase (the first polynucleotide) is operably linked to at least one regulatory sequence, such as a promoter, an enhancer, an intron, a termination sequence, or any combination thereof, and, optionally, to a second polynucleotide encoding a signal sequence, which directs the enzyme encoded by the first polynucleotide to a particular cellular location e.g., an extracellular location. Promoters can be constitutive promoters or inducible (conditional) promoters. As described herein, mutagenesis of a parent (bacterial) polynucleotide encoding a phytase was employed to prepare variant (synthetic) DNAs encoding a phytase having improved properties relative to the phytase encoded by the parent polynucleotide. In one embodiment, the mutations in a number of the variant DNAs were combined to prepare a synthetic polynucleotide encoding a phytase with enhanced thermotolerance and gastric stability and having a similar or a higher specific activity relative to the phytase encoded by the parent polynucleotide. A parent polynucleotide may be obtained from any source including plant, bacterial or fungal nucleic acid, and any method may be employed to prepare a synthetic polynucleotide of the invention from a selected parent polynucleotide, e.g., combinatorial mutagenesis, recursive mutagenesis and/or DNA shuffling.

Thus, in one embodiment of the invention, the thermotolerant phytase has one or more amino acid substitutions relative to a corresponding (reference) phytase, which substitutions are associated with the retention of activity at temperatures equal to or greater than 60° C. Preferably, the thermotolerant phytase has at least 40% activity at about 60° C. for 30 minutes, more preferably at least 40% activity at about 65° C. for 30 minutes, even more preferably at least 35% activity at 70° C. for 30 minutes, and which has a specific activity of at least 400 U/mg, more preferably at least 600 U/mg, and even more preferably at least 800 U/mg, at 37° C. and at acid pH, e.g., less than pH 5.0 and more preferably less than pH 4.0 and greater than pH 1.5. An exemplary thermotolerant phytase of the invention is provided in SEQ ID NO: 1.

Also provided by the invention are vectors which comprise the expression cassette or polynucleotide of the invention and transformed microbial cells comprising the polynucleotide, expression cassette or vector of the invention. A vector of the invention can encode more than one polypeptide including more than one thermotolerant phytase or may encode a fusion polypeptide comprising the thermotolerant phytase of the invention, and a transformed microbial cell may comprise one or more vectors of the invention. The transformed cells of the invention are useful for preparing the recombinant thermotolerant phytase of the invention. Accordingly, the invention provides thermotolerant phytase isolated from the transformed microbial cells of the invention, as well as synthetically prepared enzyme.

Further provided by the invention are methods for formulation of thermotolerant phytases, phytase formulations or formulated enzyme mixtures. The recombinant thermotolerant phytase or formulations thereof may be added as a supplement to food or animal feed or to components of food and feed prior to, during, or after food or feed processing. Preferably, the recombinant thermotolerant phytase of the invention is added to a mixture of feed components prior to and/or during heat (e.g., steam) conditioning in a pellet mill. Thus, the invention includes methods of making and using a thermotolerant phytase.

Further, as a phytase of the invention is capable of surviving the heat conditioning step encountered in a commercial pellet mill during feed formulation, the invention provides a method of making animal feed, e.g., hard granular feed pellets comprising the thermotolerant phytase. To make feed, the formulated phytase may be mixed with feed components, the mixture steam conditioned in a pellet mill such that at least 50% of the pre-heat treated enzymatic activity is retained, and the feed extruded through a pellet dye. The phytase may thus be used as a supplement in animal feed by itself, in addition with vitamins, minerals, other feed enzymes, agricultural co-products (e.g., wheat middlings or corn gluten meal), or in a combination therewith. The enzyme may also be added to mash diets, i.e., diets that have not been through a pelletizer.

Because the currently available commercial phytase enzymes are not thermotolerant, they are often applied post pelleting, generally via spraying an enzyme solution onto pelleted feed. Some of the problems associated with spraying methods are that only a low percentage of the pellets are contacted with enzyme, the enzyme is only present on the surface of the coated pellets, and feed mills need to invest in and operate complex spraying machinery. In contrast, the thermotolerant phytase of the invention, which has an 8-fold higher specific activity than other commercially available enzymes, may be added prior to pelleting, thereby facilitating production of a feed with an improved distribution of the enzyme. Moreover, feed comprising the thermotolerant phytase of the invention may have a longer shelf life than feed sprayed with phytase, as the spraying process introduces moisture which can support fungal and bacterial growth during storage. Further, the higher specific activity of the thermotolerant phytase of the invention allows feed manufacturers to use significantly lower phosphate levels in feed. For example, it is currently recommended that diets supplemented with the available commercial phytases use a basal level of 0.45% inorganic phosphate. The thermotolerant phytase of the invention may be used with a lower phosphate supplementation, e.g., about 0.225% in poultry diets.

The invention thus provides a method of preparing animal feed comprising providing a mixture comprising one or more feed components and a preparation comprising the thermotolerant phytase of the invention, and treating the mixture under appropriate conditions of temperature and moisture so as to hydrolyze phytic acid which is present in the mixture. Also provided is animal feed prepared by such a method. Further provided is a method of preparing a thermotolerant phytase containing composition for feed formulation comprising combining a liquid solution comprising the thermotolerant phytase of the invention and meal flour, e.g., soy meal flour, to yield a mixture; and lyophilizing the mixture to yield a lyophilized composition.

The invention further provides a method in which a mixture comprising animal feed components and a preparation comprising the thermotolerant phytase of the invention is treated with heat so as to yield a heat-treated animal feed mixture. Heat-treated animal feed prepared by the method is also provided. The phytase preparation may be a liquid or a solid preparation, and preferably comprises less than about 1% inorganic phosphate. In one embodiment, a liquid solution comprising the thermotolerant phytase of the invention is combined with soy meal flour to yield a mixture and the mixture is then lyophilized. The mixture, which preferably comprises less than 0.45% inorganic phosphate, may also comprise at least one vitamin, mineral, an enzyme other than a thermotolerant phytase, an organic acid, a probiotic product, an essential oil or a grain processing co-product. The heat-treated feed may be further processed, for example, by extruding the heat-treated feed through a pellet mill to yield pelletized animal feed. Also provided is an animal feed composition comprising the thermotolerant phytase of the invention, and an enzyme feed additive or a food additive comprising such a thermotolerant phytase.

Also provided is a method of decreasing the feed conversion ratio and increasing the weight gain of an animal comprising feeding to an animal a feed comprising the thermotolerant phytase. Further provided is a method of minimizing dietary requirements of phosphorus, e.g., inorganic phosphorous, in an animal. The method comprises feeding to an animal a feed comprising the thermotolerant phytase of the invention in an amount effective to increase the bioavailability of phosphorus, preferably the bioavailability of inorganic phosphorous, in the feed to the animal. Also provided is a method of enhancing the utilization of phosphorus present in feed for an animal, which method comprises feeding to the animal a feed comprising the thermotolerant phytase of the invention in an amount effective to increase the bioavailability of phosphorus in the feed to the animal.

In addition, the invention provides a method of decreasing the phosphate levels in excreta from an animal comprising feeding to the animal a feed comprising less than 0.45% inorganic phosphorus and the thermotolerant phytase of the invention in an amount effective to lower levels of phosphate in the excreta of the animal.

The invention provides a method of improving the nutritive value of animal feed or human food. The method comprises adding the thermotolerant phytase of the invention during the preparation of animal feed or human food. Also provided is a method of preparing human food comprising providing a mixture of a food component and a preparation comprising the thermotolerant phytase of the invention; and treating the mixture under appropriate conditions of temperature and moisture to facilitate the hydrolysis of phytic acid present in the mixture.

Animals within the scope of the invention include polygastric animals, e.g., calves, as well as monogastric animals such as swine, poultry (e.g., chickens, turkeys, geese, ducks, pheasant, grouse, quail and ostrich), equine, ovine, caprine, canine and feline, as well as fish and crustaceans. The levels of phytase in feed or food are preferably about 50 to 5000 U/kg, more preferably 100 to 1200 U/kg, or 300 to 1200 U/kg.

BRIEF DESCRIPTION OF THE FIGURES

FIG. 4 shows the gastric stability half-lives and residual activity following 5 minutes at 95° C. in aqueous solution of mutant NOV9X derived from expression in various hosts.

DETAILED DESCRIPTION OF THE INVENTION

Definitions

Figure 1A:
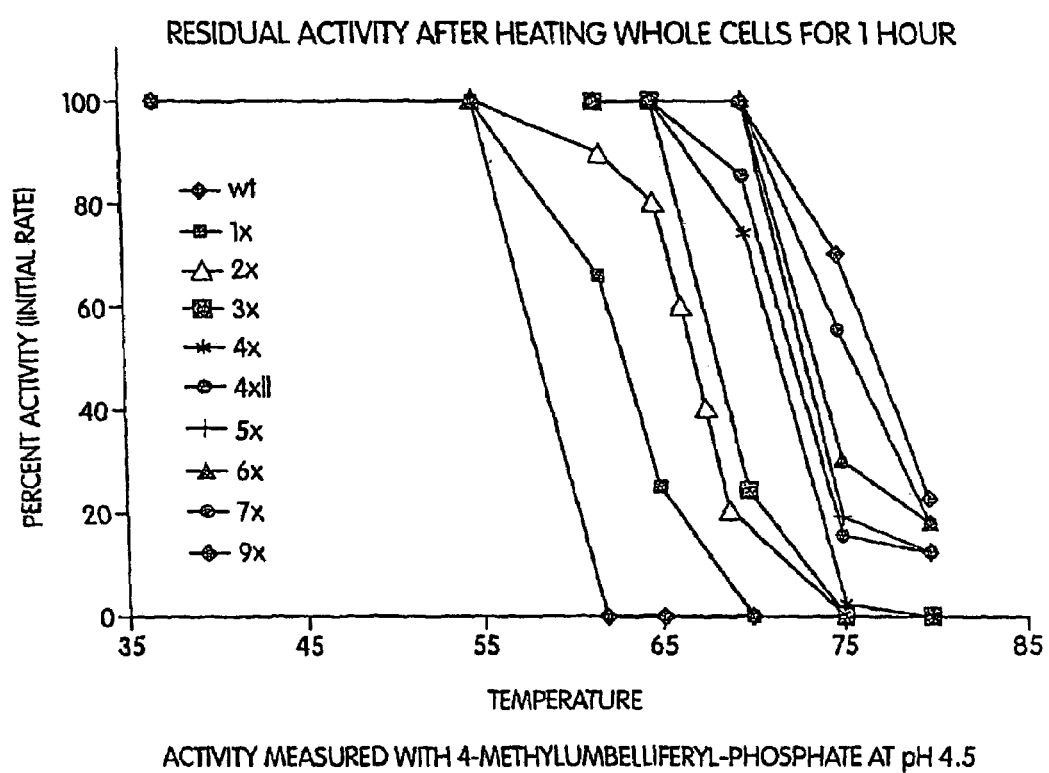
FIG. 1A illustrates the residual phytase activity after heating whole *E. coli* cells having wild-type or mutant phytase genes for one hour at various temperatures. Mutants prepared by Gene Site Saturation Mutagenesis ("GSSM") developed by Diversa Corporation and having specific amino acid substitutions are designated 1x–4x, 4x11, 5x–7x (which have one mutation or up to eight individual amino acid substitutions) and NOV9X (which has all eight amino acid substitutions, see SEQ ID NO:1). 1B illustrates the NOV9X phytase amino acid sequence showing the 8 mutations in bold and underlined.

A "microbial" host cell as used herein refers to a bacterium, yeast and fungus.

"Altered levels" refers to the level of expression in transformed or transgenic cells or organisms that differs from that of normal or untransformed cells or organisms.

"Antisense inhibition" refers to the production of antisense RNA transcripts capable of suppressing the expression of protein from an endogenous gene or a transgene.

"Chimeric" is used to indicate that a DNA sequence, such as a vector or a gene, is comprised of more than one DNA sequences of distinct origin which are fused together by recombinant DNA techniques resulting in a DNA sequence, which does not occur naturally. The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide resistance to antibiotics such as tetracycline, hygromycin or ampicillin, or other means for selection of transformed cells.

"Coding sequence" refers to a DNA or RNA sequence that codes for a specific amino acid sequence and excludes the non-coding sequences which are 5' and 3' to the coding sequence. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

"Constitutive expression" refers to expression using a constitutive or regulated promoter. "Conditional" and "regulated expression" refer to expression controlled by a regulated promoter.

The term "contacting" may include any method known or described for introducing a nucleic acid segment into a cell.

"Expression" refers to the transcription and/or translation of an endogenous gene or a transgene in a host cell. For example, in the case of antisense constructs, expression may refer to the transcription of the antisense DNA only. In addition, expression refers to the transcription and stable accumulation of sense (mRNA) or functional RNA. Expression may also refer to the production of protein.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus.

The "expression pattern" of a promoter (with or without enhancer) is the pattern of expression levels. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis. Northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Genetically stable" and "heritable" refer to chromosomally-integrated genetic elements that are stably maintained in the host cell and stably inherited by progeny through successive generations.

"Genome" refers to the complete genetic material of an organism.

The terms "heterologous DNA sequence," "exogenous DNA segment" or "heterologous polynucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

"Inducible promoter" refers to those regulated promoters that can be turned on in a cell by an external stimulus, such as a chemical, light, hormone, stress, or a pathogen.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

The term "intracellular localization sequence" refers to a nucleotide sequence that encodes an intracellular targeting signal. An "intracellular targeting signal" is an amino acid sequence that is translated in conjunction with a protein and directs it to a particular sub-cellular compartment. "Endoplasmic reticulum (ER) stop transit signal" refers to a carboxy-terminal extension of a polypeptide, which is translated in conjunction with the polypeptide and causes a protein that enters the secretory pathway to be retained in the ER. "ER stop transit sequence" refers to a nucleotide sequence that encodes the ER targeting signal.

The invention encompasses isolated or substantially purified nucleic acid or protein compositions. In the context of the present invention, an "isolated" or "purified" polynucleic acid (polynucleotide) segment or an "isolated" or "purified" polypeptide is a polynucleic acid segment or polypeptide that, by the hand of man, exists apart from its native environment and is therefore not a product of nature. An isolated polynucleic acid segment or polypeptide may exist in a purified form or may exist in a non-native environment such as, for example, a transgenic host cell. For example, an "isolated" or "purified" polynucleic acid segment or protein, or biologically active portion thereof, is substantially free of other cellular material, or culture medium when produced by recombinant techniques, or substantially free of chemical precursors or other chemicals when chemically synthesized. Preferably, an "isolated" polynucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active fragment (e.g., catalytically) thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" is intended a portion of the nucleotide sequence or a portion of the amino acid sequence, and hence a portion of the polypeptide or protein, encoded thereby.

A "marker gene" encodes a selectable or screenable trait.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

The term "native gene" refers to gene that is present in the genome of an untransformed cell.

"Naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

The term "polynucleotide", "nucleic acid", "polynucleic acid" or "polynucleic acid segment" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al., 1994).

NOV9X and Nov9X are used interchangeably herein.

A "nucleic acid fragment" is a fraction of a given nucleic acid molecule. Deoxyribonucleic acid (DNA) is the genetic material while ribonucleic acid (RNA) is involved in the transfer of information contained within DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene (Batzer et al., 1991; Ohtsuka et al., 1985; Rossolini et al., 1999). Expression cassettes employed to introduce a phytase encoding open reading frame of the invention to a host cell preferably comprise a transcriptional initiation region linked to the open reading frame. Such an expression cassette may be provided with a plurality of restriction sites for insertion of the open reading frame and/or other DNAs, e.g., a transcriptional regulatory regions and/or selectable marker gene(s).

The transcriptional cassette will include in the 5'-3' direction of transcription, a transcriptional and translational initiation region, the DNA sequence of interest, and a transcriptional and translational termination region functional in a microbial cell. The termination region may be native with the transcriptional initiation region, may be native with the DNA sequence of interest, or may be derived from another source.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably linked" when used with respect to nucleic acid, means joined as part of the same nucleic acid molecule, suitably positioned and oriented for transcription to be initiated from the promoter. DNA operably linked to a promoter is "under transcriptional initiation regulation" of the promoter. Coding sequences can be operably-linked to regulatory sequences in sense or antisense orientation. When used with respect to polypeptides, "operably linked" means joined as part of the same polypeptide, i.e., via peptidyl bonds.

"Overexpression" refers to the level of expression in transgenic cells or organisms that exceeds levels of expression in normal or untransformed cells or organisms.

Known methods of polymerase chain reaction "PCR" include, but are not limited to, methods using paired primers, nested primers, single specific primers, degenerate primers, gene-specific primers, vector-specific primers, partially mismatched primers, and the like. See also Innis et al., 1995; and Gelfand, 1995; and Innis and Gelfand, 1999.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

Promoter elements, particularly a TATA element, that are inactive or that have greatly reduced promoter activity in the absence of upstream activation are referred to as "minimal or core promoters." In the presence of a suitable transcription factor or factors, the minimal promoter functions to permit transcription. A "minimal or core promoter" thus consists only of all basal elements needed for transcription initiation, e.g., a TATA box and/or an initiator.

The terms "protein," "peptide" and "polypeptide" are used interchangeably herein.

"Regulated promoter" refers to promoters that direct gene expression not constitutively, but in a temporally- and/or spatially-regulated manner, and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters. Some suitable regulatory sequences useful in the present invention will include, but are not limited to, constitutive promoters inducible promoters and viral promoters.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Stably transformed" refers to cells that have been selected and regenerated on a selection media following transformation.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Transcription stop fragment" refers to nucleotide sequences that contain one or more regulatory signals, such as polyadenylation signal sequences, capable of terminating transcription.

The term "transformation" refers to the transfer of a nucleic acid fragment into the genome of a host cell. Host cells containing the transformed nucleic acid fragments are referred to as "transgenic" cells.

"Transformed," "transgenic," and "recombinant" refer to a host cell such as a bacterium into which a heterologous nucleic acid molecule has been introduced. The nucleic acid molecule can be stably integrated into the genome by methods generally known in the art which are disclosed in Sambrook et al., 1989). For example, "transformed," "transformant," and "transgenic" cells have been through the transformation process and contain a foreign gene, e.g., as an episomal element or integrated into their chromosome. The term "untransformed" refers to cells that have not been through the transformation process.

A "transgene" refers to a gene that has been introduced into the genome by transformation and is stably maintained. Transgenes may include, for example, genes that are either heterologous or homologous to the genes of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host cell but that is introduced by gene transfer.

"Transiently transformed" refers to cells in which an expression cassette, polynucleotide or transgene has been introduced but not selected for stable maintenance.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

A polypeptide or enzyme exhibiting "phytase" activity or a "phytase" is intended to cover any enzyme capable of effecting the liberation of inorganic phosphate or phosphorous from various myo-inositol phosphates. Examples of such myo-inositol phosphates (phytase substrates) are phytic acid and any salt thereof, e.g., sodium phytate or potassium phytate or mixed salts. Also any stereoisomer of the mono-, di-, tri-, tetra- or penta-phosphates of myo-inositol may serve as a phytase substrate. In accordance with the above definition, the phytase activity can be determined using any assay in which one of these substrates is used. A thermotolerant phytase of the invention includes variant polypeptides derived from a particular thermotolerant phytase by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the thermotolerant phytase. Such variants may result from, for example, from human manipulation. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, 1985; Kunkel et al., 1987; U.S. Pat. No. 4,873,192; Walker and Gaastra, 1983, and the references cited therein. Guidance as to appropriate amino acid substitutions that do not affect biological activity of the protein of interest may be found in the model of Dayhoff et al., 1978, herein incorporated by reference. Conservative substitutions, such as exchanging one amino acid with another having similar properties, are preferred.

Thus, the thermotolerant phytase genes and nucleotide sequences of the invention include both the naturally occurring sequences as well as mutant forms. Likewise, the thermotolerant phytase polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. Nevertheless, one skilled in the art will appreciate that the effect will be evaluated by routine screening assays. The nucleic acid molecules of the invention can be optimized for enhanced expression in a host cell of interest. It is recognized that all or any part of the gene sequence may be optimized or synthetic. That is, synthetic or partially optimized sequences may also be used. Variant nucleotide sequences and proteins also encompass sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, 1994; Stemmer, 1994; Crameri et al., 1997; Moore et al., 1997; Zhang et al., 1997; Crameri et al., 1998; and U.S. Pat. Nos. 5,605,793 and 5,837,458.

By "variants" is intended substantially similar sequences. For nucleotide sequences, variants include those sequences that, because of the degeneracy of the genetic code, encode the identical amino acid sequence of the reference protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the reference protein, as well as those that encode a polypeptide having amino acid substitutions. Generally, nucleotide sequence variants of the invention will have at least 40%, 50%, 60%, preferably 70%, more preferably 80%, even more preferably 90%, most preferably 99%, and single unit percentage identity to the native nucleotide sequence based on these classes. For example, 71%, 72%, 73% and the like, up to at least the 90% class. Variants may also include a full length gene corresponding to an identified gene fragment.

"Vector" is defined to include, inter alia, any plasmid, cosmid, phage or other vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

Preferred Constructs and Host Cells of the Invention

The invention preferably provides an expression cassette which comprises a nucleic acid sequence (promoter) capable of directing expression of a polynucleotide encoding a thermotolerant phytase either in vitro or in vivo. Methods to prepare and/or identify a thermotolerant phytase include mutagenesis, e.g., recursive mutagenesis, and/or selection or screening, e.g., for phytases having activity at temperatures greater than 60° C. Methods for mutagenesis and nucleotide sequence alterations are well known in the art. See, for example, Kunkel, 1985; Kunkel et al., 1987; U.S. Pat. No. 4,873,192; Walker and Gaastra, 1983 and the references cited therein; and Arnold et al., 1996.

A. DNA and Host Cells for Transformation

Vectors, plasmids, cosmids, YACs (yeast artificial chromosomes) BACs (bacterial artificial chromosomes) and DNA segments for use in transforming cells will generally comprise the phytase encoding DNA, as well as other DNA such as cDNA, gene or genes which one desires to introduce into the cells. These DNA constructs can further include structures such as promoters, enhancers, polylinkers, or even regulatory genes as desired. One of the DNA segments or genes chosen for cellular introduction will often encode a protein which will be expressed in the resultant transformed (recombinant) cells, such as will result in a screenable or selectable trait and/or which will impart an improved phenotype to the transformed cell. However, this may not always be the case, and the present invention also encompasses transformed cells incorporating non-expressed transgenes.

DNA useful for introduction into cells includes that which has been derived or isolated from any source, that may be subsequently characterized as to structure, size and/or function, chemically altered, and later introduced into cells. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Such DNA is commonly referred to as "recombinant DNA."

Therefore useful DNA includes completely synthetic DNA, semi-synthetic DNA, DNA isolated from biological sources, and DNA derived from introduced RNA. Generally, the introduced DNA is not originally resident in the genotype which is the recipient of the DNA, but it is within the scope of the invention to isolate a gene from a given genotype, and to subsequently introduce multiple copies of the gene into the same genotype, e.g., to enhance production of a given gene product.

The introduced DNA includes, but is not limited to, DNA from genes such as those from bacteria, yeasts, fungi, or viruses. The introduced DNA can include modified or synthetic genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of the untransformed cell.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the transformed cell. For example, the DNA may itself comprise or consist of a promoter that is active in a cell which is derived from a source other than that cell, or may utilize a promoter already present in the cell that is the transformation target.

Generally, the introduced DNA will be relatively small, i.e., less than about 30 kb to minimize any susceptibility to physical, chemical, or enzymatic degradation which is known to increase as the size of the DNA increases. The number of proteins, RNA transcripts or mixtures thereof which is introduced into the cell is preferably preselected and defined, e.g., from one to about 5–10 such products of the introduced DNA may be formed.

The selection of an appropriate expression vector will depend upon the host cells. Typically an expression vector contains (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a gene of interest that is operatively linked to the DNA elements to control transcription initiation. The expression vector used may be one capable of autonomously replicating in the above host or capable of integrating into the chromosome, originally containing a promoter at a site enabling transcription of the linked phytase gene.

If prokaryotes such as bacteria are used as the host, the expression vector for the phytase is preferably one capable of autonomously replicating in the microorganism and comprising a promoter, a ribosome-binding sequence, the novel phytase gene, and a transcription termination sequence. The vector may also contain a gene for regulating the promoter.

Yeast or fungal expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences.

Suitable vectors include by way of example: for bacteria, pQE70, pQE60, pQE-9 (Qiagen), pBluescript II (Stratagene), pTRC99a, pKK223-3, pDR540, pRIT2T (Pharmacia); for eukaryotic cells: pXT1, pSG5 (Stratagene) pSVK3, pBPV, pMSG, pSVLSV40 (Pharmacia). Such commercial vectors include, for example, pKK223-3 (Pharmacia Fine Chemicals, Uppsala, Sweden) and GEM1 (Promega Biotec, Madison, Wis., USA). However, any other plasmid or vector may be used as long as they are replicable and viable in the host.

As representative examples of appropriate hosts, there may be mentioned: bacterial cells, such as *E. coli, Streptomyces, Bacillus subtilis;* and various species within the genera *Escherichia, Pseudomonas, Serratia, Streptomyces, Corynebacterium, Brevibacterium, Bacillus, Microbacterium,* and *Staphylococcus,* although others may also be employed as a matter of choice; fungal cells belonging to the genera *Aspergillus, Rhizopus, Trichoderma, Neurospora, Mucor, Penicillium,* etc., such as yeast belonging to the genera *Kluyveromyces, Saccharomyces, Schizosaccharomyces, Trichosporon, Schwanniomyces,* and the like.

The construction of vectors which may be employed in conjunction with the present invention will be known to those of skill of the art in light of the present disclosure (see, e.g., Sambrook et al., 1989; Gelvin et al., 1990). The expression cassette of the invention may contain one or a plurality of restriction sites allowing for placement of the polynucleotide encoding a thermotolerant phytase under the regulation of a regulatory sequence. The expression cassette may also contain a termination signal operably linked to the polynucleotide as well as regulatory sequences required for proper translation of the polynucleotide. The expression cassette containing the polynucleotide of the invention may be chimeric, meaning that at least one of its components is heterologous with respect to at least one of the other components. Expression of the polynucleotide in the expression cassette may be under the control of a constitutive promoter, inducible promoter, regulated promoter, viral promoter or synthetic promoter.

The expression cassette may include in the 5'-3' direction of transcription, a transcriptional and translational initiation region, the polynucleotide of the invention and a transcriptional and translational termination region functional in vivo and/or in vitro. The termination region may be native with the transcriptional initiation region, may be native with the polynucleotide, or may be derived from another source. The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences which may be a combination of synthetic and natural sequences.

The vector, used in the present invention may also include appropriate sequences for amplifying expression.

B. Regulatory Sequences

A promoter is a nucleotide sequence which controls the expression of a coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may contain DNA sequences that are involved in the binding of protein factors which control the effectiveness of transcription initiation in response to physiological or developmental conditions. A promoter may also include a minimal promoter plus a regulatory element or elements capable of controlling the expression of a coding sequence or functional RNA. This type of promoter sequence contains of proximal and more distal elements, the latter elements are often referred to as enhancers.

Representative examples of promoters include, but are not limited to, promoters known to control expression of genes in prokaryotic or eukaryotic cells or their viruses. Particular bacterial promoters include *E. Coli* lac or trp, the phage lambda $P_L$, lacI, lacZ, T3, T7, gpt, and lambda $P_R$ promoters.

Any promoter capable of expressing in yeast hosts can be used as the promoter. Examples thereof include promoters for genes of hexokinase and the like in the glycolytic pathway, and promoters such as gal 1 promoter, gal 10 promoter, heat shock protein promoter, MFa-1 promoter and CUP 1 promoter.

Any promoter capable of expressing in filamentous fungi may be used. Examples are a promoter induced strongly by starch or cellulose, e.g., a promoter for glucoamylase or a-amylase from the genus *Aspergillus* or cellulase (cellobiohydrase) from the genus *Trichoderma*, a promoter for enzymes in the glycolytic pathway, such as phosphoglycerate kinase (pgk) and glycerylaldehyde 3-phosphate dehydrogenase (gpd), etc.

Two principal methods for the control of expression are known, viz.: overexpression and underexpression. Overexpression can be achieved by insertion of one or more than one extra copy of the selected gene. For underexpression there are two principle methods which are commonly referred to in the art as "antisense downregulation" and "sense downregulation". Generically these processes are referred to as "gene silencing". Both of these methods lead to an inhibition of expression of the target gene.

Several inducible promoters are known in the art. Many are described in a review by Gatz (1996) (see also Gatz, 1997). Examples include tetracycline repressor system, Lac repressor system, copper-inducible systems, salicylate-inducible systems (such as the PR1a system), glucocorticoid-inducible (Aoyama T. et al., 1997) and ecdysome-inducible systems. Also included are the benzene sulphonamide-inducible (U.S. Pat. No. 5364,780) and alcohol-inducible (WO 97/06269 and WO 97/06268) inducible systems and glutathione S-transferase promoters.

Regulated expression of a chimeric transacting viral replication protein can be further regulated by other genetic strategies. For example, Cre-mediated gene activation as described by Odell et al., 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al., 1997. Again, either the chimeric tRNA suppressor gene, the chimeric transacting replication gene, or both can be under the control of developmental-specific or inducible promoters.

In addition to the use of a particular promoter, other types of elements can influence expression of transgenes. In particular, introns have demonstrated the potential for enhancing transgene expression.

Other elements include those that can be regulated by endogenous or exogenous agents, e.g., by zinc finger proteins, including naturally occurring zinc finger proteins or chimeric zinc finger proteins. See, e.g., U.S. Pat. No. 5,789, 538, WO 99/48909; WO 99/45132; WO 98/53060; WO 98/53057; WO 98/53058; WO 00/23464; WO 95/19431; and WO 98/54311.

An enhancer is a DNA sequence which can stimulate promoter activity and may be an innate element of the promoter or a heterologous element inserted to enhance the level or tissue specificity of a particular promoter. An enhancer is capable of operating in both orientations (5' to 3' and 3'-5' relative to the gene of interest coding sequences ), and is capable of functioning even when moved either upstream or downstream from the promoter. Both enhancers and other upstream promoter elements bind sequence-specific DNA-binding proteins that mediate their effects.

Vectors for use in accordance with the present invention may be constructed to include an enhancer element. Constructs of the invention will also include the gene of interest along with a 3' end DNA sequence that acts as a signal to terminate transcription and allow for the polyadenylation of the resultant mRNA.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure.

C. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., an antibiotic, or the like), or whether it is simply a trait that one can identify through observation or testing, i.e., by 'screening'. Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA and small active enzymes detectable in extracellular solution.

Selectable markers for use in prokaryotes include a tetracycline resistance or an ampillicin resistance gene. Screenable markers that may be employed include, but are not limited to, a b-glucuronidase or uidA gene (GUS) which encodes an enzyme for which various chromogenic substrates are known; a beta-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an alpha-amylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a beta-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

Transformation

The expression cassette, or a vector construct containing the expression cassette, may be inserted into a cell. The expression cassette or vector construct may be carried episomally or integrated into the genome of the cell, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any vector may be used as long as it is replicable and viable in the host.

A variety of techniques are available and known to those skilled in the art for introduction of constructs into a cellular host. Transformation of microbial cells may be accomplished through use of polyethylene glycol, calcium chloride, viral infection, DEAE dextran, phage infection, electroporation and other methods known in the art. Transformation of fungus may be accomplished according to Gonni et al. (1987). Introduction of the recombinant vector into yeasts can be accomplished by methods including electroporation, use of spheroplasts, lithium acetate, and the like. Any method capable of introducing DNA into animal cells can be used: for example, electroporation, calcium phosphate, lipofection and the like.

Recombinant Enzyme

For preparation of recombinant phytase, following transformation of a suitable host strain and growth of the host strain to an appropriate cell density, e.g., a bacterial or yeast host, a selected promoter may be induced by appropriate means (e.g., temperature shift or chemical induction) and cells cultured for an additional period to yield recombinant enzyme. Cells are then typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a product of chemical synthetic procedures, or produced by recombinant techniques from a microbial host (for example, by bacterial, yeast, and fungal cells in culture). Depending upon the host employed in a recombinant production procedure, the enzyme of the present invention may or may not be covalently modified via glycosylation. In eukaryotic cells, glycosylation of secreted proteins serves to modulate protein folding, conformational and thermostability stability, and resistance to proteolysis. Given a specific application of phytase use, a glycosylated version of the enzyme may be preferable over a non-glycosylated form. For example, the use of a glycosylated phytase in animal feed helps protect the enzyme from thermal denaturation during feed pelleting and from proteolytic inactivation as it passes through the stomach of the animal, helping deliver active enzyme to the intestinal tract and site of action. For food processing applications where enzyme activity is desired only during processing and not in the final product a non-glycosylated, thermolabile, and proteolytic susceptible phytase is preferred. By producing the phytase of this invention in various microbial hosts, both thermotolerance and susceptibility to proteolytic degradation are altered. For example, when produced in *Escherichia coli* the phytase of the present invention exhibits a half life of 8.4 minutes in simulated gastric fluid, while in *Pichia pastoris* and *Schizosaccharomyces pombe* these values increase to 10.4 and 29.2 minutes, respectively. *E. coli* does not posses the cellular machinery to glycosylate proteins, while the extent of glycosylation in *S. pombe* is greater than in *P. pastoris*. Similarly, residual activity following a 5 minute heating step at 95° C. increases with increasing degrees of glycosylation. In *E. coli* 10% residual activity is measured, while in *P. pastoris* and *S. pombe* the values increase to 30 and 50%, respectively. Enzymes of the invention may or may not also include an initial methionine amino acid residue.

The enzymes of this invention may be employed for any purpose in which such enzyme activity is necessary or desired. In a preferred embodiment, the enzyme is employed for catalyzing the hydrolysis of phytate in animal feed. In another preferred embodiment, the enzyme is employed for catalyzing the hydrolysis of phytate in food.

Phytase Compositions

Generally, phytase compositions are liquid or dry. Liquid compositions need not contain anything more than the phytase enzyme, preferably in a highly purified form. However, a stabilizer such as glycerol, sorbitol or mono propylen glycol may be added. The liquid composition may also comprise other additives, such as salts, sugars, preservatives, pH-adjusting agents, proteins, and phytate (a phytase substrate). Typical liquid compositions are aqueous or oil-based slurries. The liquid compositions may be added to a food or feed before or after an optional pelleting thereof.

Dry compositions may be freeze-dried or spray dried compositions, in which case the composition need not contain anything more than the enzyme in a dry form. Dry compositions may be granulates which may readily be mixed with, e.g., food or feed components, or more preferably, form a component of a pre-mix. The particle size of the enzyme granulates preferably is compatible with that of the other components of the mixture. This provides a safe and convenient means of incorporating enzymes into, e.g., processed food or animal feed.

For example, a stable phytase enzyme formulation can be prepared by freezing a mixture of liquid enzyme solution with a bulking agent such as ground soybean meal, and then lyophilizing the mixture. The reduction in moisture and the binding interactions of the phytase with the bulking agent protect the enzyme from external environmental factors such as the temperature extremes experienced during compound feed manufacture. Dry formulations can further enhance stability by minimizing the activity of potential proteolytic enzymes that may be present as by-products in the liquid fermentation mixture used to manufacture the target enzyme. The resulting dry enzyme-soy flour mixture of the present invention can withstand high extremes of temperature. For example, after 120 minutes of heating at 96° C., the dry enzyme formulation retained 97.8% of its original enzymatic activity. This formulated enzyme mixture can be used as a feed supplement for use in poultry and swine production. For instance, addition of 500 enzyme units of a thermotolerant phytase of the invention to 1 kg of a standard corn-soy poultry diet allowed a reduction in the levels of inorganic phosphate supplementation currently used in animal nutrition, i.e., from 0.45% to 0.225%. Chickens raised on a 0.225% phosphate diet supplemented with the formulated phytase performed as well as birds fed a standard diet containing 0.45% phosphate. Moreover, a reduction in phosphate supplementation results in decreased levels of phosphate pollution, which in turn significantly lessens the environmental impact of intensive commercial animal production.

Once a dry enzyme preparation is obtained, agglomeration granulates are prepared using agglomeration techniques in a high shear mixer during which a filler material and the enzyme are co-agglomerated to form granules. Absorption granulates are prepared by having cores of a carrier material to absorb/be coated by the enzyme. Typical filler materials are salts such as disodium sulphate. Other fillers include kaolin, talc, magnesium aluminium silicate and cellulose fibres. Optionally, binders such as dextrins are also included in agglomeration granulates.

Typical carrier materials include starch, e.g., in the form of cassava, corn, potato, rice and wheat. Salts may also be used.

Optionally, the granulates are coated with a coating mixture. Such a mixture comprises coating agents, preferably hydrophobic coating agents, such as hydrogenated palm oil and beef tallow, and if desired, other additives such as calcium carbonate or kaolin.

Additionally, phytase compositions may contain other substituents such as coloring agents, aroma compounds, stabilizers, vitamins, minerals, other feed or food enhancing enzymes and the like. This is so in particular for the so-called pre-mixes.

A "food or feed additive" is an essentially pure compound or a multi component composition intended for or suitable for being added to food or feed. In particular it is a substance that by its intended use is becoming a component of a food or feed product or affects any characteristics of a food or feed product. Thus, a phytase additive is understood to mean a phytase which is not a natural constituent of the main feed or food substances or is not present at its natural concentration therein, e.g., the phytase is added to the feed separately from the feed substances, alone or in combination with other feed additives. A typical additive usually comprises one or more compounds such as vitamins, minerals or feed enhancing enzymes and suitable carriers and/or excipients.

A "ready for use" phytase additive is herein defined as an additive that is not produced in situ in animal feed or in processed food. A ready for use phytase additive may be fed to humans or animals directly or, preferably, directly after mixing with other feed or food constituents. For example, a feed additive according to this aspect of the present invention is combined with other feed components to produce feed. Such other feed components include one or more other (preferably thermostable) enzyme supplements, vitamin feed additives, mineral feed additives and amino acid feed additives. The resulting (combined) feed additive including possibly several different types of compounds can then be mixed in an appropriate amount with the other feed components such as cereal and protein supplements to form an animal feed. Processing of these components into an animal feed can be performed using any of the currently used processing apparatuses such as a double-pelleting machine, a steam pelleter, an expander or an extruder.

Similarly, a food additive according to this aspect of the present invention is combined with other food components to produce processed food products. Such other food components include one or more other (preferably thermostable) enzyme supplements, vitamin food additives and mineral food additives. The resulting (combined) food additive, including possibly several different types of compounds can then be mixed in an appropriate amount with the other food components such as cereal and plant proteins to form a processed food product. Processing of these components into a processed food product can be performed using any of the currently used processing apparatuses.

In a preferred embodiment, the phytase compositions of the invention additionally comprises an effective amount of one or more feed or food enhancing enzymes, in particular feed or food enhancing enzymes selected from the group consisting of alpha-galactosidases, beta-galactosidases, in particular lactases, other phytases, beta-glucanases, in particular endo-beta-1,4-glucanases and endo-beta-1,3(4)-glucanases, cellulases, xylosidases, galactanases, in particular arabinogalactan endo-1,4-beta-galactosidases and arabinogalactan endo-1,3-beta-galactosidases, endoglucanases, in particular endo-1,2-beta-glucanase, endo-1,3-alpha-glucanase, and endo-1,3-beta-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-alpha-rhamnosidase, pectate lyases, and alpha-galacturonisidases, mannanases, beta-mannosidases, mannan acetyl esterases, xylan acetyl esterases, proteases, xylanases, arabinoxylanases and lipolytic enzymes such as lipases, phospholipases and cutinases.

The animal feed additive of the invention is supplemented to the animal before or simultaneously with the diet. Preferably, the animal feed additive of the invention is supplemented to the animal simultaneously with the diet.

An effective amount of phytase in food or feed is from about 10 to 20,000 FTU/kg; preferably from about 10 to 15,000 FTU/kg, more preferably from about 10 to 10,000 FTU/kg, in particular from about 100 to 5,000 FTU/kg, especially from about 100 to about 2,000 FTU/kg feed or food.

Also within the scope of this invention is the use of phytase for processing and manufacturing human foods and animal feeds. Grains and flours destined for human foods can be enzymatically treated with phytase to reduce the phytin content of the material. The reduced levels of phytin enhance the quality of the food by increasing the nutrient availability of essential minerals such as iron, calcium, and zinc. In addition to increasing the nutritional quality of food, phytase used during food processing can improve the overall efficiency of the food production method. For example, addition of phytase to white soybean flakes during soy protein isolate manufacturing can significantly increase the yield and quality of extractable protein. During food manufacture the phytase is active during manufacture and processing only, and is not active in the final food product. This aspect is relevant for instance in dough making and baking. Similarly, animal feed grains such as toasted soybean meal or canola meal may be pre-processed with phytase prior to compound feed manufacture. Removal of the anti-nutritive factors in animal feed components prior to compound feed manufacture produces a nutritionally higher quality and more valuable animal feed ingredient. In this processing method the phytase is active during feed manufacturing, and may or may not be active in the digestive tract of the animal upon ingestion of the treated feed.

In addition to using phytase as a food processing aid, the scope of this invention encompasses the use of phytase as a human supplemental digestive aid. Phytase in tablet form can be ingested at the time of food consumption to deliver active enzyme to the gastrointestinal tract of the recipient. Nutritional gains for the consumer would be experienced in vivo and may be taken with foods that cannot be treated with a phytase during food processing.

Also within the scope of the invention is the use of a phytase of the invention during the preparation of food or feed preparations or additives, i.e., the phytase is active during the manufacture only and is not active in the final food or feed product. This aspect is particularly relevant, for instance, in dough making and baking and the production of other ready-to-eat cereal based products.

The phytase may also be used advantageously in monogastrics as well as in polygastrics, especially young calves. Diets for fish and crustaceans may also be supplemented with phytase to further improve feed conversion ratio and reduce the level of excreted phosphorus for intensive production systems. The feed according to the present invention may also be provided to animals such as poultry, e.g., turkeys, geese, ducks, as well as swine, equine, bovine, ovine, caprine, canine and feline, as well as fish and crustaceans. It is however, particularly preferred that the feed is provided to pigs or to poultry, including, but not limited to, broiler chickens, hens, in particular laying hens, turkeys and ducks.

Feed Compositions and Methods of Use

The phytases (formulated as described above) of the current invention may be combined with other ingredients to result in novel feed compositions with particular advantages.

For instance, it is preferable that intensive animal production operations limit the phosphate pollution that is contained in the feces of the animals that are produced. The amount of phosphate present in the diet and the availability of the phosphate in the diet to the animal are the primary factors influencing the excreted phosphate present in the feces of the animal. Currently, the availability of the plant, or grain-derived phosphate, present in soybean meal, corn grain (and other feedstuffs) is low as the phosphate is primarily in the form of phytic acid. In order to maximize the growth efficiencies of the animals inorganic phosphate is added to feed resulting in a feed composition that contains adequate levels of available phosphate. However, these feed formulations contain too much total phosphate and result in phosphate pollution.

Although commercially available phytases at present result in higher phosphate availability they are recommended to be used with high levels of added inorganic phosphate. The phytases of the present invention are so active that they can be used to create novel animal feed formulations that have a) significantly reduced levels of inorganic phosphate, and b) allow superior feed conversion efficiency and improved weight gain relative to normal diets. At present, commercially available phytases will not allow animals to be efficiently produced on a feed that contains no added inorganic phosphorus Specifically, the animal feed of the invention comprises the combination of a phytase of the present invention in combination with animal feed ingredients to form a feed that has substantially lowered inorganic phosphorus levels. In a preferred embodiment, the feed compositions of the invention comprises typical feed ingredients, micronutrients, vitamins, etc. and an effective amount of thermostable phytase and inorganic phosphate where the amounts of the phytase and phosphorus are from about between the levels of 50–20,000 units of phytase per kg of feed and less than 0.45% inorganic phosphorus; preferably between the levels of 100–10,000 units of phytase per kg of feed and less than 0.225% inorganic phosphorus; in particular between the levels of 150–10,000 units of phytase per kg of feed and less than 0.15% inorganic phosphorus, or especially between the levels of 250–20,000 units of phytase per kg of feed and no exogenously added inorganic phosphorus.

Also, within the scope of the invention are methods of improving weight gains, and feed conversions ratios (FCR) associated with production of farm animals. A phytase of the present invention allows improved weight gains and FCR especially when used in combination with diets that are low in inorganic phosphate. Specifically the method of the present invention to improve the FCR, or weight gain of a low inorganic phosphate diet by feeding a diet to an animal comprising a phytase of the present invention and a level of inorganic phosphate at or below the level of 0.45%. Preferably, the method comprises feeding a diet containing the phytase and less than 0.225% inorganic phosphate, or most preferably the method comprises feeding a diet containing the phytase and no added inorganic phosphorus.

The animal feed of the present invention can be used on monogastric or polygastric animals. The animal feed of the present invention can be feed for poultry, or swine, or calves, or companion animals such as dogs or cats or horsed. Examples of such feed and the use of the feed are provided in Example 3.

The present invention also provides for a method of animal husbandry that results in a significantly reduced environmental phosphate load. The method comprises feeding entire flocks or herds of farm animals a feed composition containing a phytase of the present invention and a reduced amount of inorganic phosphorus (less than 0.45%). More preferably the method comprises feeding entire flocks or herds of farm animals a feed composition containing a phytase of the present invention and a significantly reduced amount of inorganic phosphorus (less than 0.225%), or most preferably the method comprising feeding entire flocks or herds of farm animals a feed composition containing a phytase of the present invention and no inorganic phosphorus. This method will allow high densities of animals to be maintained while minimizing the environmental release of phosphate from the farming operation.

The invention will be further described by the following examples, which are not intended to limit the scope of the invention in any manner.

EXAMPLE 1

Exemplary Methods to Prepare and Identify Thermotolerant Phytases Recombinant Expression For expression in *Aspergillus niger*, *A. niger* NW205 (ura-arg-nic-) may be transformed and screened for phytase-producing transformants as described in Passamontes et al. (1997).

For expression in *Saccharomyces cerevisiae,* a phytase gene is cloned into a 2μ-based vector, such as one harboring a shortened version of the gap(FL) promoter and the pho5 terminator (Janes et al., 1990) as well as a selection marker. The phytase gene is cloned downstream of the gap(FL) promoter in the EcoRI-BamHI blunt-ended expression cassette. *S. cerevisiae* YMR4 (urg$^-$ his$^-$ leu$^-$ pho3$^-$ pho5$^-$) is used for transformation. Individual transformants are grown initially for 1 to 2 days in minimal medium. Phytase production is tested after subsequent culture for 2 to 3 days in YPD medium.

For expression in *Hansenula polymorpha*, the phytase gene may be cloned as an EcoRI fragment into the corresponding site of the *H. polymorpha* expression vector pFP (Gellisen et al., 1991) downstream of the formate dehydrogenase (FMD) promoter (EPA 299108). The resulting plasmid is transformed into *H. polymorpha* RB11. Transformants are individually inoculated into minimal medium (YNB containing 2% glucose). After several passages under selective pressure to force multiple integrations of the expression plasmids into the genome of *H. polymorpha*, single stable clones are tested for phytase activity.

For expression in *Pichia*, a pPIcαA vector encoding a phytase is transformed into *P. pastoris* strain X33 by electroporation according to the manufacturer's instructions (Invitrogen). The transformed cells are plated into YPD-Zeocin agar medium and positive colonies are incubated in minimal medium with glycerol (BMGY) for 24 hours. When the yeast cell density reaches $2.5 \times 10^8$ cells/ml ($OD_{600}=5$), the cells are centrifuged and suspended in 0.5% methanol medium (BMMY) to induce gene expression.

Protein Purification

Culture broths (typically 500 to 1,000 ml) are centrifuged to remove cells and concentrated by ultrafiltration with Amicon 8400 cells (PM30 membranes; Grace Ag, Wallisellen, Switzerland) and ultrafree-15 centrifugal filter devices (Biomax-30K; Millipore, Bedford, Mass.). The concentrates (typically 1.5 to 5 ml) are desalted with either Fast Desalting HR 10/10 or Sephadex G-25 Superfine columns (Pharmacia Biotech, Dubendorf, Switzerland) using 10 mM sodium acetate (pH 5.0) as the elution buffer. The desalted samples are directly loaded onto a 1.7 ml Poros HS/M catio-exchange chromatography column (PerSeptive Biosystems, Framingham, Mass.) or onto a 1.7-ml Poros HQ/M anion-exchange chromatography column. During both anion-exchange and cation-exchange chromatography, phytase is eluted in pure form by using an optimized sodium chloride gradient.

Desalted phytases expressed in yeast such as *S. cerevisiae* or *S. pombe* are brought to 2 M $(NH_4)_2SO_4$ after desalting and loaded onto a 1-ml Butyl Sepharose 4 Fast Flow hydrophobic interaction chromatography column (Pharmacia Biotech). The enzymes are eluted with a linear 2 to 0 M $(NH_4)_2SO_4$ gradient in 20 mM sodium acetate (pH 5.0). The phytases eluted in the breakthrough and are concentrated and loaded onto a 120-ml Sephacryl S-300 gel permeation chromatography column (Pharmacia Biotech).

For enzymes expressed in *Pichia*, the enzymes are initially suspended into 50 mM Tris-HCl, pH 7, and ammonium sulfate is added to 25% of saturation. After the mixture is centrifuged (25,000 g, 20 minutes), the pellet is suspended into 10 mL of 25 mM Tris-HCl, pH 7. The suspension is dialyzed overnight against the same buffer and loaded onto a DEAE-Sepharose column (Sigma) equilibrated with 25 mM Tris-HCl pH 7. Proteins are eluted with 0.2 M NaCl, 25 mM Tris-HCl, pH 7, after the column is washed with 200 mL of 25 mM Tris-HCl, pH 7. All the collected fractions are assayed for phytase activity and protein concentration (Lowry et al., 1951). The whole purification is conducted at 4° C., and the fractions are stored at −20° C.

Estimation of Phytase Activity

Determination of phytase activity, based upon the estimation of inorganic phosphate released on hydrolysis of phytic acid, can be performed at 37° C. following the method described by Engelen et al. (2001). One unit of enzyme activity is defined as the amount of enzyme that liberates 1 μmol of inorganic phosphate per minute under assay conditions. For example, phytase activity may be measured by incubating 2.0 ml of the enzyme preparation with 4.0 ml of 9.1 mM sodium phytate in 250 mM sodium acetate buffer pH 5.5, supplemented with 1 mM $CaCl_2$ for 60 minutes at 37° C. After incubation, the reaction is stopped by adding 4.0 ml of a color-stop reagent consisting of equal parts of a 10% (w/v) ammonium molybdate and a 0.235% (w/v) ammonium vanadate stock solution. Phosphate released is measured against a set of phosphate standards spectrophotometrically at 415 nm. Phytase activity is calculated by interpolating the $A_{415}$ nm absorbance values obtained for phytase containing samples using the generated phosphate standard curve. Alternatively, a phytase activity curve generated by using a standardized phytase reference whose activity is certified by the manufacturer may be used in place of a phosphate standard curve to determine enzymatic activity. Specific activity can be expressed in units of enzyme activity per mg of protein.

Alternatively, determination of phytase activities, based on the estimation of inorganic phosphate released on hydrolysis of phytic acid, can be performed at 37EC following the method described by Engelen et al. (1994). One unit of enzyme activity is defined as the amount of enzyme that liberates 1 μmol of inorganic phosphate per minute under assay conditions. For example, phytase activity may be measured by incubating 150 ml of the enzyme preparation with 600 ml of 2 mM sodium phytate in 100 mM Tris HCl buffer pH 7.5, supplemented with 1 mM $CaCl_2$ for 30 minutes at 37° C. After incubation, the reaction is stopped by adding 750 ml of 5% trichloroacetic acid. Phosphate released is measured against phosphate standard spectrophotometrically at 700 nm after adding 1500 ml of the color reagent (4 volumes of 1.5% ammonium molybdate in 5.5% sulfuric acid and 1 volume of 2.7% ferrous sulfate; Shimizu, 1992). Alternatively, phytase activity is measured in an assay mixture containing 0.5% (about 5 mM) phytic acid and 200 mM sodium acetate (pH 5.0). After 15 minutes of incubation at 37° C. (or at temperatures between 37 and 90° C.), the reaction is stopped by adding an equal volume of 15% trichloroacetic acid. The liberated phosphate ions are quantified by mixing 100 ml of the assay mixture with 900 ml of $H_2O$ and 1 ml of 0.6 M $H_2SO_4$-2% ascorbic acid-0.5% ammonium molybdate. After 20 minutes of incubation at 50° C., absorbance at 820 nm is measured. Specific activity can be expressed in units of enzyme activity per mg of protein.

pH Behavior

For the study of pH behavior, phytase is diluted in 200 mM Na-acetate buffer, pH 5.5. Substrate solution is prepared in one of the following buffers: 200 mM glycine, pH 2.0, 2.5 or 3.0; 200 mM Na-acetate buffer, pH 3.5, 4.0, 4.5, 5.0, 5.5, 6.0 or 6.5 and 200 mM Tris-HCl, pH 7.0, 7.5, 8.0, 8.5 or 9.0. All buffers are supplemented with 1 mM $CaCl_2$. The substrate solution contained 10 mM phytic acid from rice ($C_6H_6O_{24}Na_{12}$; Sigma-Aldrich Chemie GmbH, Steinheim, Germany).

Two milliliters of enzyme preparation are preincubated in a water bath at the assay temperature for 5 minutes, and the enzyme reactions are initiated by adding 4 ml of the substrate solution. Since the mixing ratio slightly alters the pH of the mixture, the pH of the mixture is adjusted to the desired pH before incubation. The mixture is incubated for a period, e.g., 60 minutes, at a temperature of 37EC. The incubation is terminated by adding 4 ml of molybdovanadate reagent. The reagent is prepared as described by Engelen et al. (1994). Then the activities of the enzyme is determined.

Thermal Behavior

For the determination of the optimum temperature curves, preparation of enzyme and substrate solutions, as well as their mixing ratio are as described above. However, the pH of the mixtures correspond to the determined optimum pH. The mixtures are incubated for a period, e.g., 60 minutes, at one or more of the following temperatures: 30, 40, 50, 55, 60, 65, 70, 75, 80 and 100°C. The activity is measured on the basis of inorganic orthophosphate released. For thermostability study in aqueous solutions, phytases may be pre-incubated at elevated temperatures. After the preincubation periods, the samples are cooled on ice for 30 minutes. They were reincubated at 37°C and the residual activities of the enzyme determined.

Thermal stability in aqueous media does not properly reflect stability in the feed pelleting process. For an enzyme to be attractive for widespread application as feed additive, it should be able to withstand temperature conditions necessary for pre-treatment of feeds. One common pre-treatment of animal feeds is pelleting. For thermostability study in feed mixtures, a practical diet containing wheat as a major ingredient and fortified with vitamins and minerals may be chosen for pelleting experiments at different pelleting temperatures. Since wheat contains an appreciable quantity of native phytase activity, the diet is first pelleted at different temperatures in order to measure the inactivation of the native phytase activity. Heat treatments are varied by modifying the steam introduction into the conditioner and temperatures are adjusted in the conditioner (noting that the temperature of the die will increase for 7 to 10° C. above the temperature in the conditioner). Temperature control in the conditioner is made continuously by a sensor incorporated in the machine. For pelleting, a die with holes of 5 mm diameter and 15 mm length is used. For calculating the residual activity of added phytases, the native phytase activity at each temperature treatment is subtracted from the total activity. The pellets are cooled subsequently in a batch cooler. Samples of the resulting pellets are analyzed for the level of phytase activity remaining relative to that added to the meal and taking into consideration native phytase activity at each temperature treatment. Most broiler and piglet diets are pelleted at temperatures around 70°C.

Resistance to Protease Inactivation

The resistance of the phytases to protease inactivation may be investigated using pepsin from porcine stomach mucosa and pancreatin from porcine pancrease. The pepsin, Sigma P7012 (Sigma-Aldrich Chemie GmbH, Steinheim, Germany) contained 2,500 to 3,500 units of activity per mg protein and the pancreatin, Sigma P1500, from the same source, contained activity equivalent to the United States Pharmacopeia (U.S.P.). Pepsin is suspended with 0.1 M HCl (pH 2.0) and pancreatin is dispersed in 0.1 M NaHCO$_3$ (pH 7.0).

For assays with pepsin, 1 ml of a freshly prepared pepsin solution containing 3000 U/ml is mixed with 1 ml of a freshly prepared phytase solution (0.02 and 0.08 U/2 ml after dilution with buffer at the final stage of measuring phytase activity) in a test tube. The mixture is incubated for 0 to 45 minutes in a waterbath at 37°C and pH 2.0 (optimum conditions for pepsin activity). After incubation, 1 ml of the solution is diluted (1:9) with buffer solution (pH 5.5) and thoroughly mixed. Two ml of the solution is incubated with 4 ml phytic acid substrate solution for 60 minutes at 40°C and pH 5.5 and phytase activity is determined. For assays with pancreatin, 1 ml of a freshly prepared pancreatin solution containing 4.81 mg/ml is mixed with 1 ml of phytase solution. The mixture is incubated for 0 and 45 minutes at 40°C and pH 7.0. Dilutions and pH adjustments for phytase activity measurements are the same as described above.

Alternatively, the purified phytase (2 mg/ml) is incubated with different amounts of pepsin and trypsin following the manufacturer instructions (Sigma). Pepsin (800 U/mg protein) and trypsin (1500 BAEE units/mg protein) are dissolved into 10 mM HCl, pH 2 (0.1 mg/mL), respectively. One BAEE unit is defined as 0.001 absorbance change at 253 nm per minute at pH 7.6 and 25° C., with BAEE as a substrate. In a final volume of 100 mL, 10 mg of purified phytase (0.08 to 0.1 U) is incubated with trypsin or pepsin at protease/phytase (w/w) ratios ranging from 0.001 to 0.01, at 37° C. for 1 to 120 minutes. The reaction is stopped on ice and the pH of the mixture was adjusted to 8 for protein electrophoresis and phytase activity assay. The digested protein mixtures were analyzed by sodium dodecyl sulfate (SDS)-polyacrylamide or urea-SDS-polyacrylamide gel electrophoresis.

Stability in Digesta Supernatants

Digesta samples are collected from laying hens. The birds are killed by cervical dislocation and their digestive tracts are removed. Digesta samples were collected from crop, stomach (proventriculus), duodenum (pylorus to entrance of bile ducts), jejunum (bile ducts entracts to Meckel's diverticulum), and ileum (Meckel's diverticulum to the ileocecal junction). The pH of the digested samples are determined using a digital pH meter (Ingol Messtechnik AG, Urdorf, Switzerland). The pH readings of the various segments are 5.02, 2.75, 6.28, 6.63 and 6.98 for crop, stomach, duodenum, jejunum and ileum, respectively.

The samples are either frozen at −20°C until use or used immediately. Digesta samples are diluted 1:1 in distilled water, mixed thoroughly and centrifuged a 10,000 g for 10 minutes. Supernatants are recovered and their pH values are adjusted to correspond to the initial pH values of the different segments of the digestive tract. The recovered digesta supernatants are held in an ice/waterbath until use. For assays, 1 ml of digesta supernatants is mixed with 1 ml of enzyme solution and the mixture is incubated for 0 and 20 minutes at 40°C. For measuring residual phytase activity, 1 ml of the solution is diluted (1:9) with buffer solution (pH 5.5). Two ml of the solution is then mixed with 4 ml of substrate solution and incubated for 60 minutes at 40°C.

EXAMPLE 2

Isolation and Identification of Thermotolerance Phytases

Gene discovery and enzyme optimization, e.g., by combining desirable mutations and/or via DNA shuffling, were employed to identify desired phytase genes. Thermotolerant phytases were selected and/or optimized for desired activity profiles. These include, for example, a high specific activity (e.g., ≧800 U/mg at pH 4.5 at 37° C. using as a substrate phytic acid including derivatives thereof, i.e., myoinositol having from 1 to 6 phosphate groups, activity at a particular temperature (e.g., 37° C.), activity at low pH (e.g., a pH optimum between 2.5 to 3.5 or less than 4.0 for swine), gastric stability (e.g., half-life >30 minutes in simulated or actual gastric fluid of poultry and swine), process stability (e.g., half-life ≧5 minutes at 85° C. in formulated state, 50% retention of at least activity through commercially acceptable pelletization process), lower use rate (e.g., effective dose of less than 0.5 gram enzyme/ton of feed results in phosphate liberation of more than 75%), and/or substrate specificity (e.g., activity on myo-inositol monophosphate).

A. New Phytases Genes

To identify new phytase genes, a number of different approaches were used. In one approach, direct cloning of appA genes from 14 different *E. coli* K-12 strains resulted in 2 new phytase genes, each with 2 amino acid differences.

Figure 2:
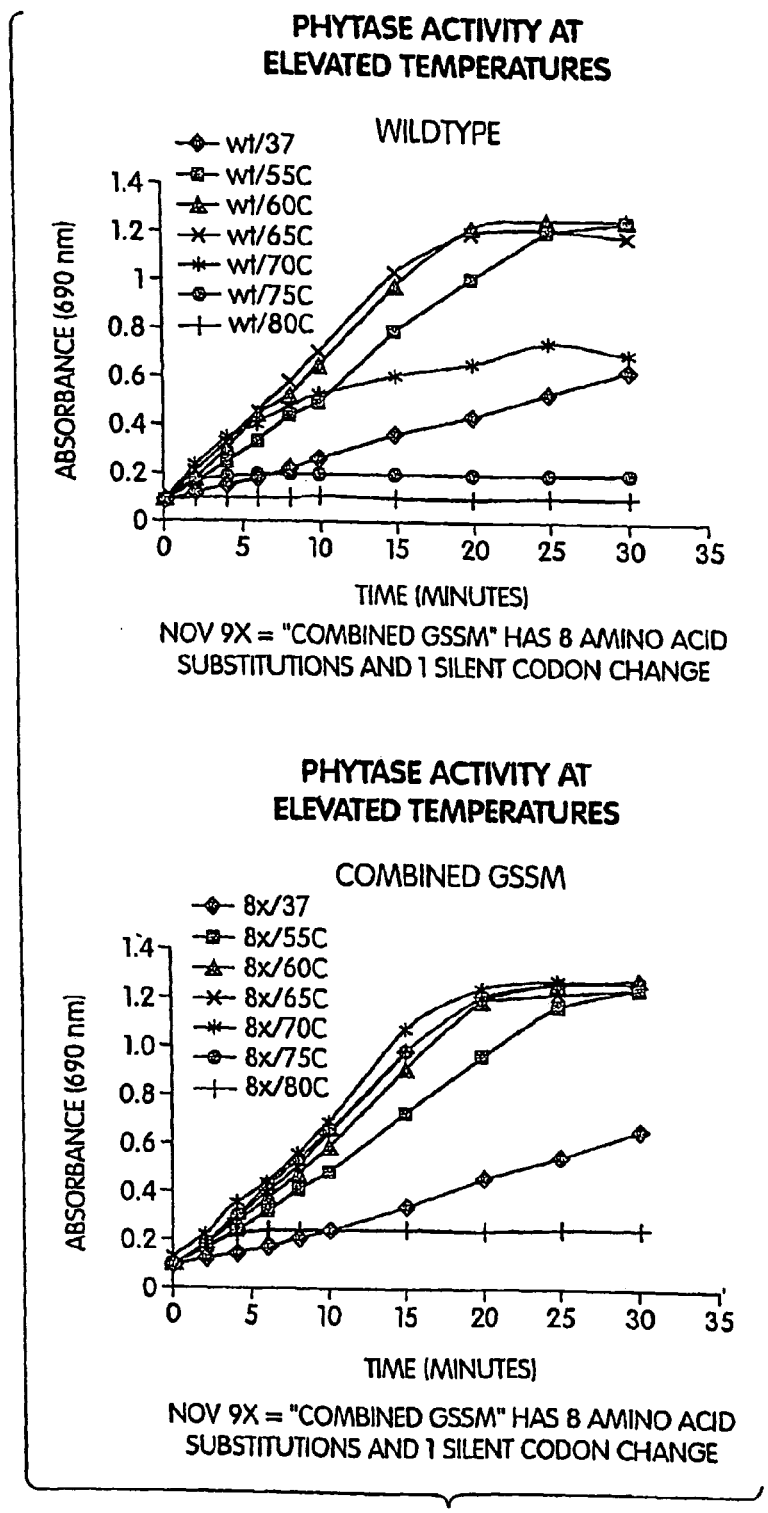
FIG. 2 shows wild-type and mutant NOV9X(SEQ ID NO:1) phytase activity in aqueous solution at elevated temperatures versus time.
Figure 3A:
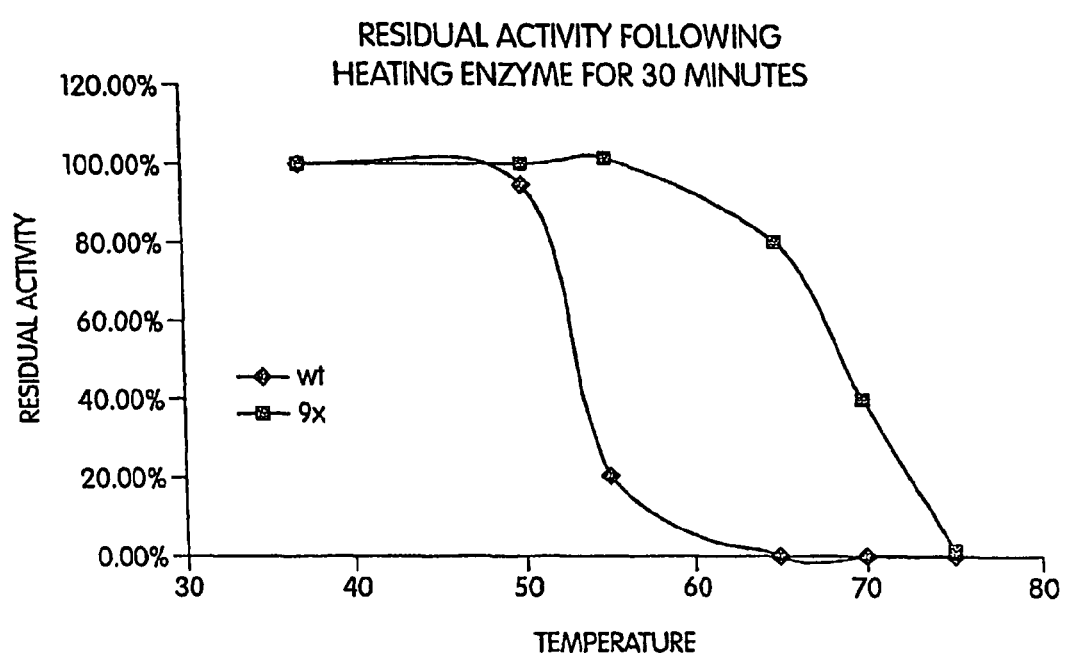
FIG. 3A illustrates the residual phytase activity of wild-type and mutant NOV9X enzyme after heating for 30 minutes in aqueous solution at various temperatures.
Figure 3B:
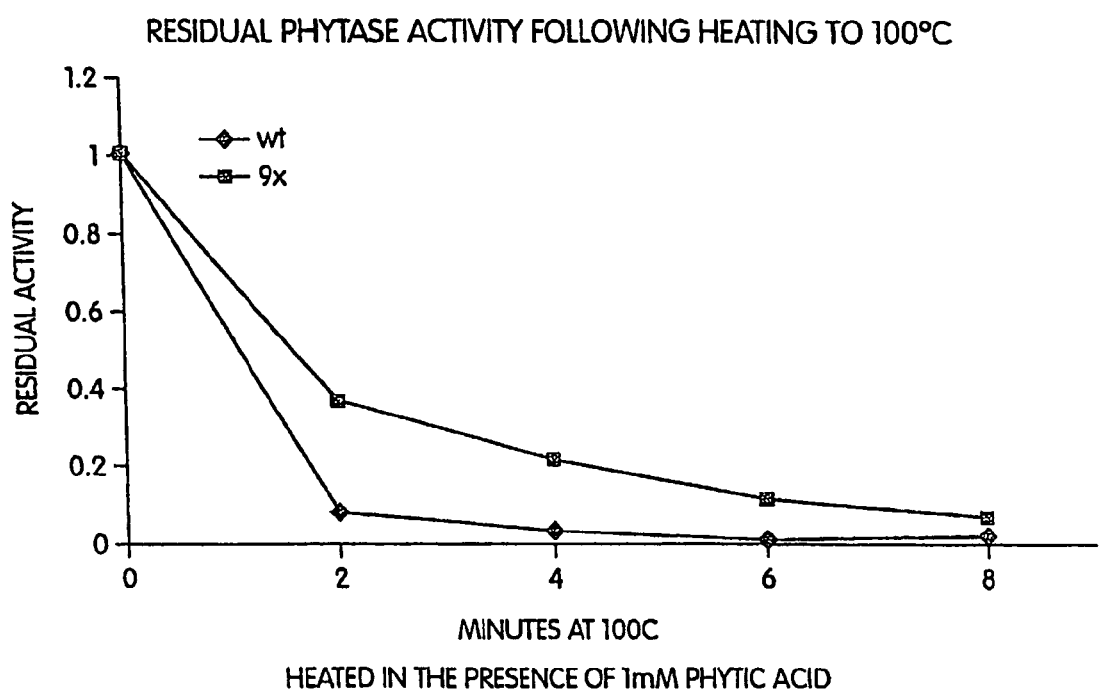
FIG. 3B illustrates the residual phytase activity of wild-type and mutant NOV9X enzyme after heating at 100° C. in aqueous solution for up to 8 minutes.

To optimize an *E. coli* phytase (appA) (parent) gene, a saturation mutagenesis was performed in which every codon in the gene was altered to encode all amino acids. (See, e.g., WO 01/90333, Diversa Corporation). All mutants were tested for residual activity after heating (70° C.). Sixteen unique clones were identified which had enhanced thermotolerance relative to the parent gene. Individual mutations were combined in a combinatorial manner, clones prepared for each combination and the clones were tested for thermal tolerance relative to wild-type *E. coli* phytase (FIGS. 1 and 2). The residual activity profile for clone NOV9X, which has 8 amino acid substitutions and one silent codon change, after 30 minutes at various temperatures is shown in FIG. 3A and at 100° C. is shown in FIG. 3B. Table 1 summarizes the properties of various phytases.

TABLE 1

| Property | AppA | NatuPhos | Nov9x | appA-2* |
|---|---|---|---|---|
| SA# | 10 | 1 | 10 | 10 |
| Thermal Stability | 3% at 100° C. | ND | 40% at 100° C. | ND | relative at pH 4.5

The gastric stability and thermal tolerance of the NOV9X phytase expressed in various host cells is shown in FIG. 4. NOV9X phytase was produced in three different microorganisms, *E. coli*, *Pichia pastoris,* and *Schizosaccharomyces pombe*. *E. coli* does not glycosylate proteins, while *Pichia* glycosylates proteins to some degree and *S. pombe* even more so. An increasing degree of glycosylation appeared to be associated with improved gastric stability. The data also showed that thermotolerance increased with the degree of glycosylation. This effect has not been observed with other types of phytases. For example, Wyss et al. (1999) reported that the extent of differential glycosylation had no effect on fungal phytase (*A. fumigatus*) thermostability. Similarly, Rodriguez et al. (2000) reported no enhanced thermostability of an *E. coli* phytase (expressed in *Pichia pastoris*) that was genetically modified to yield higher degrees of glycosylation. Thus, the phytase NOV9X has a number of desirable properties, e.g., increased thermal tolerance, high specific activity, and enhanced gastric stability.

With respect to gastric stability and glycosylation, there are only a few comparative studies in the literature with conflicting results. A paper by Rodriquez et al. (1999) discloses that the parent *E. coli* phytase gene expressed in *Pichia pastoris* is very resistant to pepsin, but sensitive to proteolysis by trypsin. Conversely, Natuphos was found to be resistant to trypsin but sensitive to pepsin.

EXAMPLE 3

Construction and Overexpression of the Nov9X Gene Encoding a Polypeptide with Phytase and Acid Phosphatase Activity in *Pichia pastoris*

Gene Source and Protein Sequence. A synthetic gene encoding the Nov9X phytase amino acid sequence (reference to the Diversa patent for the Nov9X sequence) was constructed and cloned into the destination cloning vector pPCR-Nov9X. The gene sequence was designed utilizing yeast preferred codons and supplied in transformed Epicurian Coli XL1-Blue MRF' cells (Stratagene, La Jolla, Calif.).

Expression Host and Vector. *Pichia pastoris* pPIC9 expression vector and the *Pichia pastoris* GS115 strain were obtained from Invitrogen (Carlsberg, Calif.). The pPIC9 expression vector contains the alcohol oxidase 1 promoter (AOX1) and is methanol inducible. Cloning the Nov9X gene in frame with the vector's *Saccharomyces cerevisiae* α-factor prepro peptide secretion signal targets the recombinant protein for extracellular expression.

Construction of *Pichia pastoris* Transformation Vector. From a plasmid preparation of pPCR-Nov9X (Qiaprep Spin Miniprep protocol, Qiagen, Valencia, Calif.) the coding region of the target Nov9X gene was excised by restriction endonuclease digestion using Bgl II and Xba I restriction enzymes (New England Biolabs, Beverly, Mass.). A typical restriction digest was conducted at 37° C. for 60 minutes, followed by heat inactivation for 20 minutes at 65° C. The liberated 1242 base pair DNA fragment was gel purified (QIAquick Gel Extraction Kit, Qiagen, Valencia, Calif.) and used as DNA template for PCR amplification. Synthetic oligonucleotide primers 1 and 2 below (Sigma-Genosys, The Woodlands, Tex.) and PFU Turbo DNA Polymerase (Stratagene, La Jolla, Calif.) were utilized to amplify the target DNA:

Upstream Primer 1: 5'-gaaggggtat ctctcgagaa aagagaggct caatctgaac cagaattgaa gttggaatct (SEQ ID NO: 2)

Downstream Primer 2: 3'-attattcgcg gccgcctatt acaaggaaca ggctgggatt ct (SEQ ID NO:3)

A total of 30 cycles using the thermocycling profile listed below were used to amplify the Nov9X gene:

94° C. for 5 minutes-initial template denaturation
94° C. for 30 seconds-denaturation
61° C. for 30 seconds-annealing
72° C. for 90 seconds-primer extension Nov9X amplified PCR product (SEQ ID NO:4) was gel purified (QIAquick Gel Extraction Kit, Qiagen, Valencia, Calif.) and endonuclease digested with Not I and Xho I (New England Biolabs, Beverly, Mass.). *Pichia pastoris* expression vector pPIC9 (Invitrogen, Carlsbad, Calif.) was likewise prepared by endonuclease digestion with Not I and Xho I and purified by gel extraction. An overnight ligation of endonuclease cut Nov9X PCR product with linearized pPIC9 expression vector in the presence of T4 DNA ligase at 16° C. (New England Biolabs, Beverly, Mass.) and subsequent transformation into *E. coli* Top10F' competent cells (Invitrogen, Carlsbad, Calif.) produced the Nov9X yeast transformation construct. Nov9X/pPIC9 clones containing the gene of interest were identified by plasmid DNA restriction mapping with Not I and Xho I. The integrity of the Nov9X transformation construct was confirmed by DNA sequence analysis. This cloning strategy produced a construct where the Nov9X gene sequence was cloned in frame with the vector's *Saccharomyces cerevisiae* α-factor prepropeptide secretion signal for extra cellular protein expression.

Preparation of Nov9X/pPIC9DNA for Yeast Transformation. Plasmid DNA containing the Nov9X/pPIC9 expression construct was purified from a 50 mL culture of *E. coli* Top10F' cells grown up over night in LB broth that was supplemented with 100 µg/mL ampicillin. The isolated plasmid DNA was linearized by Bgl II endonuclease digestion for 60 minutes at 37° C. Following the digest Bgl II was heat-inactivated by a 20 minute incubation period at 65° C. Linearized Nov9X/pPIC9 DNA was purified by first a phenol and then a phenol-chloroform-isoamyl alcohol extraction. The DNA was precipitated from the aqueous phase of the final extract using isopropanol, centrifuged, washed with 70% ethanol, and resuspended in TE buffer (10 mM Tris-HCl, 0.1 mM EDTA, pH 8.0).

Preparation of *Pichia pastoris* GS115 Competent Cells. Yeast cells were prepared by streaking the cells onto YPD agarose plates. Following over night growth at 30° C. a single yeast colony from a YPD agarose plate was transferred to 10 mLs of YPD liquid broth and grown up over night at 30° C. From this 10 mL seed culture 100 µL were used to inoculate 500 mLs of additional YPD broth. This large scale culture was grown over night at 30° C. to an optical density of 1.25 when measured at 595 nm. The cells were harvested by centrifugation, resuspended, and treated with a series of water and sorbitol washes according to the manufacturer's recommendations (Invitrogen *Pichia* Expression Kit Instruction Manual, version L, pg 59).

Transformation of Nov9X/pPIC9 DNA into *Pichia pastoris* GS115. Bgl II restriction digested Nov9X/pPIC9 plasmid DNA (4.6 µg) was mixed with 80 µL of sorbitol treated *Pichia pastoris* GS115 cells in a 0.2 cm electroporation cuvette (Gene Pulser Cuvettes, BioRad, Hercules, Calif.) and incubated on ice for 5 minutes. The electroporation cuvette was placed into a BioRad Gene Pulser II instrument and pulsed using settings of 1.5 kV, 25 µF, and 200Ω. Ice cold sorbitol (1.0 mL) was added to the electroporation mix which was then plated out onto histidine deficient, minimal media-dextrose (MD) plates. Incubation at 30° C. for up to 3 days produced colony growth.

Screening Transformants for Phytase Expression. From the set of primary transformants plated on MD plates single colonies were inoculated and grown up over night at 30° C. in 25 mLs of BMGY broth (buffered minimal media with glycerol). Genomic DNA was purified from 2 mLs of the 25 mL BMGY liquid cultures using the YeaStar Genomic DNA Purification kit (Zymo Research, Orange, Calif.). Purified genomic DNA along with oligonucleotide primers 1 and 2 listed previously were used in a PCR screen to identify *Pichia pastoris* clones harboring our desired phytase gene. Thermocycling conditions listed above were used to test the set of genomic clones. Clones generating a PCR fragment of 1281 base pairs were further characterized for Nov9X protein expression. The remaining 23 mLs of Pichia culture from clones that tested positive for the Nov9X gene in the PCR screen were centrifuged at 2000 rpm for 10 minutes, the supernatant decanted, and the cell pellet resuspended in 10 mLs of BMMY (buffered minimal media with methanol) to induce protein expression. SDS-PAGE analysis of clarified fermentation broth following 24 hours of incubation at 30° C. identified clones which expressed Nov9X phytase. Functional activity assays measuring the release of inorganic phosphate from sodium phytase substrate confirmed phytase expressing cultures that secreted functionally active protein.

EXAMPLE 4

Feeding Trials

Mash Feed

Figure 5:
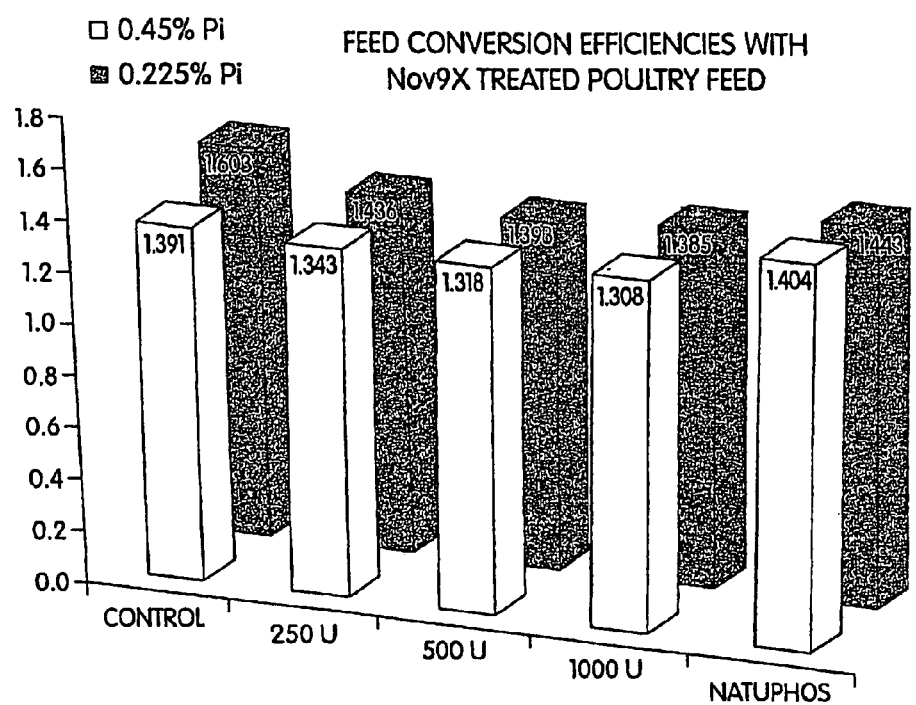
FIG. 5 illustrates feed conversion efficiencies obtained in chickens fed diets containing various levels of supplemental mutant NOV9X enzyme or Natuphos (an *Aspergillus* phytase enzyme) with different inorganic phosphate supplementations

FIG. 5 illustrates the effect of dietary inclusion of the NOV9X phytase on poultry growth performance, represented by feed conversion ratios (FCR). Feed conversion ratio refers to the amount of feed consumed divided by the net weight gain of the chicken. A lower ratio indicates that a chicken gained more weight per unit of feed consumed. A lower ratio indicates that a chicken more efficiently utilized the feed that was consumed. Standard poultry diets were used and two inorganic phosphate levels were incorporated into the diets, 0.45% and 0.225%. The 0.45% level is commonly used in commercial poultry diets. NOV9X phytase, produced in recombinant *P. pastoris* was used in this study. Replicate pens of 10 chickens for each diet were grown until 21 days of age, and final weights determined by subtracting the weight of the one day old chicks. Records were kept of the amount of feed consumed by each pen of chickens, and an average feed consumption was determined. The NOV9X phytase was formulated by freezing a mixture of liquid enzyme solution with a bulking agent, in this instance ground soybean meal, and then lyophilized. This formulation was added directly to the diets. Natuphos was used according to the manufacturer's recommendations.

The control diets (with no enzyme supplementation) clearly showed the need for phosphate supplementation. The low phosphate level gives a FCR of 1.603, while the FCR for the high phosphate control is 1.391. Adding NOV9X phytase at 250, 500, and 1000 U/kg led to an improvement in the FCRs for both the low and high phosphate diets. As more enzyme was added, the greater the improvement in the bird growth performance, as indicated by the lower FCR values. Surprisingly, given the marked reduction in phosphate in the low P diet, the 500 U/kg NOV9X low phosphate diet (FCR of 1.393) performed almost as well as the high phosphate control (FCR 1.391). Moreover, NOV9X phytase performed better than Natuphos (at 1040 U/kg), in both the high and low phosphate diets (the manufacturer of Natuphos recommends using a phosphate level of 0.45% for the positive control and reducing phosphate by only 0.1% on addition of 500 U of Natuphos). Thus, the use of the thermotolerant phytase of the invention to supplement feed reduces the levels of added phosphate needed for enhanced FCR.

Pelleted Feed

A feeding trial similar in design to that described above was performed, except that a pelleted feed was used instead of a mash diet. Feed components were mixed with either the NOV9X phytase enzyme (produced either in *P. pastoris* or in *S. pombe*) or Natuphos and then pelleted using steam injection for conditioning at 85° C. Replicate pens of chickens were fed the diets and weight gains were determined in 42 day old chickens.

Figure 6:
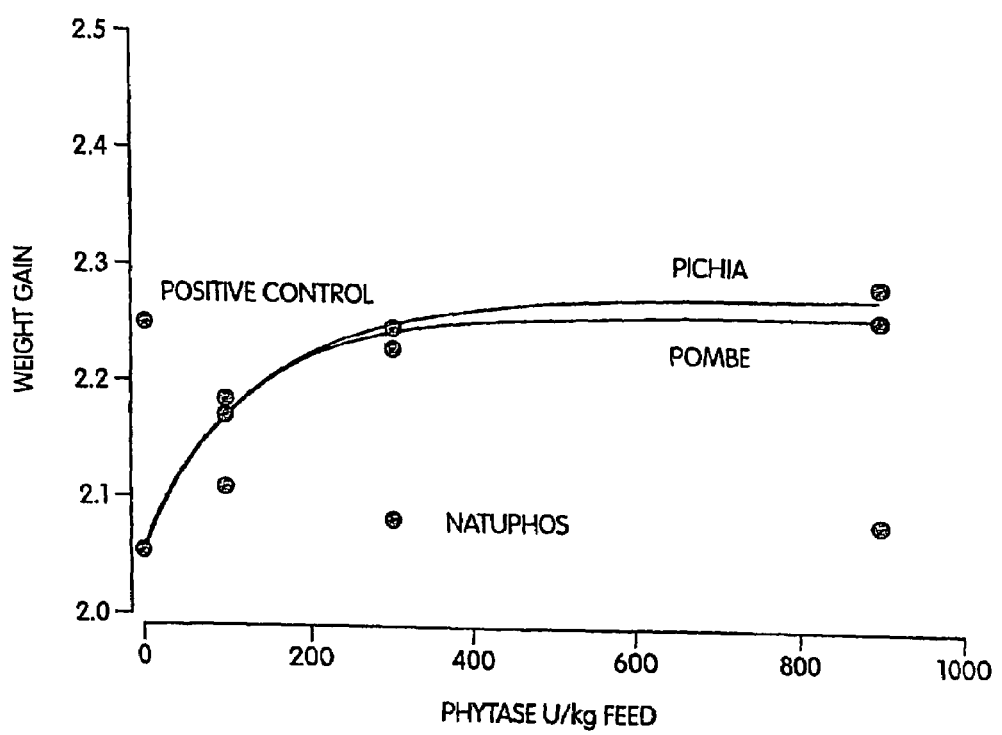
FIG. 6 shows weight gain data for chicken fed pelleted feed containing NOV9X enzyme obtained from various recombinant hosts or Natuphos.

A control diet with no added phytase contained 0.45% phosphate. All other diets (with Natuphos or NOV9X at 100, 300, and 900 units/kg) contained 0.225% phosphate. The weight gain data is shown in FIG. 6. These data show that the NOV9X phytase survived the pelletization process and resulted in improved performance of the chickens that consumed those diets. Weight gains significantly improved relative to the no enzyme control and are approximately equal to the positive control (the 0.45% high phosphate diet with no enzyme). These data also confirmed the superior performance of the NOV9X phytase relative to Natuphos with respect to thermostability.

EXAMPLE 5

Feeding Trials

Figure 7:
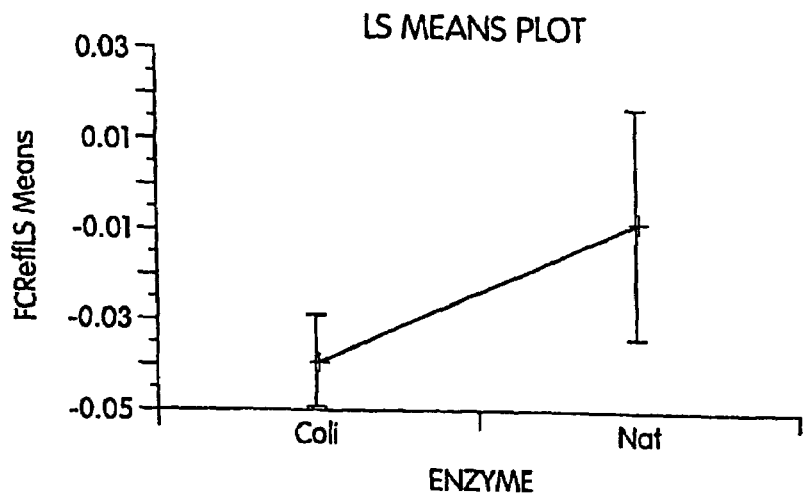
FIG. 7 shows an LS means plot of the benefit of Nov9X phytase and Natuhos from cumulative reivw of data from nine trials. FCReff LSmeans is the average benefit in points of FCR on use of the enzyme. *Coli* and Nat were significantly different p=0.0291 when the model FCReff=intercept, Enzyme (*coli* or natuphos), Dose, control FCR, maize %, dietary metabolisable energy content, diet calcium content, fat content (animal and vegetable), stocking density was employed. R-square=0.92, model p=<0.0001.
Figure 8:
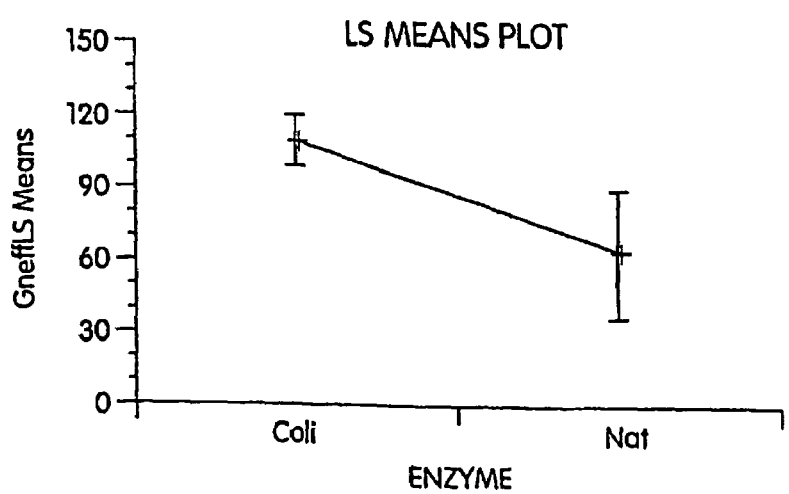
FIG. 8 shows an LS means plot of benefit of Zymetrics Nov9x phytase (*Coli*) and Natuphos (Nat) from cumulative review of data from 9 trials. Gneff LSmeans is the average benefit in grams of gain on use of the enzyme. *Coli* (benefit 109 grams) and Nat (benefit 63 grams) were significantly different from zero and from one another (p=0.0029) when the model gain effect=intercept, Enzyme (*Coli* or Natuphos), Dose, maize %, wheat %, dietary metabolisable energy content, diet total phosphorus content and lighting regimen was employed. R-square=0.94, model p=<0.0001.

Seven further trials were conducted, some to 21 days of age and others to 42 days of age. In each trial NOV9X was dosed at various levels and in most cases compared against Natuphos. Animal performance data from these 7 and the 2 trials described above were then entered into a datasheet and statistically analysed using a stepwise linear regression approach to determine which of the 35 x variables (diet, enzyme and management variables) examined described the variation in the dataset best. Significant models were described for both gain and FCR and are expressed graphically in FIGS. 7 and 8. Enzyme source (i.e., Natuphos or NOV9X) proved to be a significant determinant of the gain and fer variation measured. NOV9X therefore proved to be superior to Natuphos on average, over the 9 trials entered in the dataset, in terms of both gain and fcr. Such a multi-factorial or meta-analyis approach is more reliable in determining relative efficacies of products since undue reliance on one trial is avoided.

Taken collectively, the data in this example indicate that the NOV9X phytase was significantly more effective at liberating organic phosphate that is present in the soybean and corn portions of the feed. When NOV9X phytase is used, it is clear animal performance can be maintained with the addition of less inorganic phosphate than is necessary in the presence of natuphos. This suggests that there will be a net reduction on phosphorus in the manure with use of NOV9X compared with Natuphos when diets are formulated to take advantage of capabilities of each product.

Additionally, these results indicate that novel compound animal feeds with low inorganic phosphate levels can be used to efficiently produce farm animals in a geographically intense manner while significantly reducing the environmental release of phosphate in the excreta of the animal. This means that farms producing these animals will have less of an environmental impact.

REFERENCES

Batzer et al., *Nucleic Acid Res.*, 19:5081 (1991).
Crameri et al., *Nature Biotech.*, 15:436 (1997).
Crameri et al., *Nature*, 391:288 (1998).
Dayhoff et al., *Atlas of Protein Sequence and Structure*, Natl. Biomed. Res. Found., Washington, C. D. (1978)
Engelen, A. J. et al., *J. AOAC. Inter.*, 77, 760 (1994).
Engelen, A. J. et al., *J. AOAC. Inter.*, 84, 629 (2001).
Gatz, *Current Opinion in Biotechnology*, 7:168 (1996).
Gatz, C., *Annu. Rev. Plant Physiol. Plant Mol. Biol.*, 48:89 (1997).
Gelfand, eds., *PCR Strategies* (Academic Press, New York (1995).
Gelvin et al., *Plant Molecular Biology Manual* (1990).
Ikuta et al., *Biotech.*, 8:241 (1990).
Innis and Gelfand, eds., *PCR Methods Manual* (Academic Press, New York) (1999).
Innis et al., eds., *PCR Protocols: A Guide to Methods and Applications* (Academic Press, New York (1995).
Jongbloed et al., *Enzymes in Animal Nutrition. Proc. of the 1st Symp. Kartause Ittingen*, Wenk, C. and Boessinger, M. (Eds.), Switzerland, pp. 173–180 (1993).
Katz et al., *J. Gen. Microbiol.*, 129:2703 (1983).
Kornegay, E. T. et al., *Brit. J. Nutr.*, 75, 839 (1996).
Kunkel et al., *Methods in Enzymol.*, 154:367 (1987).
Kunkel, *Proc. Natl. Acad. Sci. USA*, 82:488 (1985).
Moore et al., *J. Mol. Biol.*, 272:336 (1997).
Mroz, Z. et al., *J. Anim. Sci.* 72, 126 (1994).
Munro et al., *Cell*, 48, 899 (1987).
Niedz et al., *Plant Cell Reports*, 14: 403 (1995).
Odell et al. *Mol. Gen. Genet.*, 113:369 (1990).
Ohtsuka et al., *J. Biol. Chem.*, 260:2605 (1985).
Ow et al., *Science*, 234:856 (1986).
Pallauf, J. and Rimbach, G., *Arch. Anim. Nutr.*, 50, 301 (1997).
Prasher et al., *Biochem. Biophys. Res. Comm.*, 126:1259 (1985).
Rao, R. S. V. et al., *Anim. Feed Sci. Technol.*, 79, 211 (1999).
Ravindran, V. et al., *Poult. Sci.*, 78, 699 (1999).
Rodriguez et al., *Arch. Biochem. Biophy.*, 365:262 (1999).
Rodriguez et al., *Arch. Biochem.,Biophy.*, 382:105 (2000).
Rossolini et al., *Mol. Cell. Probes*, 8:91 (1994).
Sambrook et al., *Molecular Cloning: A Laboratory Manual* (2d ed., Cold Spring Harbor Laboratory Press, Plainview, N.Y.) (1989).
Stemmer, *Nature*, 370:389 (1994).
Stemmer, *Proc. Natl. Acad. Sci. USA*, 91:10747 (1994).
Sutcliffe, *PNAS USA*, 75:3737 (1978).
Turner et al., *Molecular Biotechnology*, 3:225 (1995).
Walker and Gaastra, eds., *Techniques in Molecular biology*, MacMillan Publishing Company, New York (1983).
Wyss et al., *App. Environ. Micro.*, 65:359 (1999).
Zhang et al., *Proc. Natl. Acad. Sci. USA*, 94:4504 (1997).
Zukowsky et al., *PNAS USA*, 80:1101 (1983).

All cited publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A method to prepare a thermotolerant phytase, comprising:
   expressing in a microbial host cell an expression cassette comprising a promoter operably linked to a nucleic acid molecule encoding a thermotolerant phytase which retains at least 40% activity after 30 minutes at 60° C. and has a specific activity of greater than 200 U/mg at pH 4.5 and 37° C. wherein the thermotolerant phytase comprises the polypeptide sequence depicted in SEQ ID NO.1 or a variant polypeptide thereof having a deletion or substitution of one or more amino acids from the N-terminal and/or C-terminal of said polypeptide sequence;
   and obtaining the expressed thermotolerant phytase by disrupting the microbial host cells.

2. The method of claim 1 further comprising isolating the thermotolerant phytase.

3. The method of claim 1, wherein the host cell is a bacterial cell.

4. The method of claim 1, wherein the host cell is *Escherichia, Pseudomonas, Lactobacillus,* or *Bacillus.*

5. The method of claim 1, wherein the host cell is a yeast cell.

6. The method of claim 1, wherein the host cell is a *Kluyveromyces, Saccharomyces, Schizosaccharomyces, Trichosporon, Schwanniomyces, Pichia* or *Hansuel* cell.

7. The method of claim 1, wherein the host cell is a *Saceharomyces cerevisiae, Pichia Pastoris, Hansenula polymorpha* or *Schizosaccharomyces pombe* cell.

8. The method of claim 1, wherein the host cell is a fungal cell.

9. The method of claim 1, wherein the host cell is *Aspergillus, Rhizopus, Trichoderma, Neurospora, Mucor* or *Penicillium* cell.

10. The method of claim 1, wherein the host cell is an *Aspergillus niger* cell.

11. The method of claim 1 wherein the nucleic acid molecule comprises the nucleic acid sequence depicted in SEQ ID NO.4 encompassed by the restriction enzyme sites Xho1 and Not1.

12. The method of claim 1 wherein the thermotolerant phytase has a specific activity of greater than 400 U/mg at pH 4.5 and 37° C.

13. The method of claim 1 wherein the thermotolerant phytase has a specific activity of greater than 600 U/mg at pH 4.5 and 37° C.

14. The method of claim 1 wherein the thermotolerant phytase has a specific activity of greater than 800 U/mg at pH 4.5 and 37° C.

15. The method of claim 1 wherein the nucleic acid encodes a fusion polypeptide comprising the thermotolerant phytase.

16. The method of claim 15 wherein the fusion polypeptide comprises a signal sequence which is operably linked to the thermotolerant phytase.

17. The method of claim 1 wherein the thermotolerant phytase has a simulated gastric half life of greater than 25 minutes at a pH greater than 2.0 and less than 4.0.

18. The method of claim 1 wherein the thermotolerant phytase is glycosylated.

* * * * *

SEQUENCE LISTING

<160> NUMBER OF SEQ ID NOS: 4

<210> SEQ ID NO 1
<211> LENGTH: 412
<212> TYPE: PRT
<213> ORGANISM: Artificial Sequence
<220> FEATURE:
<223> OTHER INFORMATION: Nov9X Phytase

```
<400> SEQUENCE: 1

Met Ala Gln Ser Glu Pro Glu Leu Lys Leu Glu Ser Val Val Ile Val
1               5                   10                  15

Ser Arg His Gly Val Arg Ala Pro Thr Lys Ala Thr Gln Leu Met Gln
            20                  25                  30

Asp Val Thr Pro Asp Ala Trp Pro Thr Trp Pro Val Lys Leu Gly Glu
        35                  40                  45

Leu Thr Pro Arg Gly Gly Glu Leu Ile Ala Tyr Leu Gly His Tyr Trp
    50                  55                  60

Arg Gln Arg Leu Val Ala Asp Gly Leu Leu Pro Lys Cys Gly Cys Pro
65                  70                  75                  80

Gln Ser Gly Gln Val Ala Ile Ile Ala Asp Val Asp Glu Arg Thr Arg
                85                  90                  95

Lys Thr Gly Glu Ala Phe Ala Ala Gly Leu Ala Pro Asp Cys Ala Ile
            100                 105                 110

Thr Val His Thr Gln Ala Asp Thr Ser Ser Pro Asp Pro Leu Phe Asn
        115                 120                 125

Pro Leu Lys Thr Gly Val Cys Gln Leu Asp Asn Ala Asn Val Thr Asp
    130                 135                 140

Ala Ile Leu Glu Arg Ala Gly Gly Ser Ile Ala Asp Phe Thr Gly His
145                 150                 155                 160

Tyr Gln Thr Ala Phe Arg Glu Leu Glu Arg Val Leu Asn Phe Pro Gln
                165                 170                 175

Ser Asn Leu Cys Leu Lys Arg Glu Lys Gln Asp Glu Ser Cys Ser Leu
            180                 185                 190

Thr Gln Ala Leu Pro Ser Glu Leu Lys Val Ser Ala Asp Cys Val Ser
        195                 200                 205

Leu Thr Gly Ala Val Ser Leu Ala Ser Met Leu Thr Glu Ile Phe Leu
    210                 215                 220

Leu Gln Gln Ala Gln Gly Met Pro Glu Pro Gly Trp Gly Arg Ile Thr
225                 230                 235                 240

Asp Ser His Gln Trp Asn Thr Leu Leu Ser Leu His Asn Ala Gln Phe
                245                 250                 255

Asp Leu Leu Gln Arg Thr Pro Glu Val Ala Arg Ser Arg Ala Thr Pro
            260                 265                 270

Leu Leu Asp Leu Ile Lys Thr Ala Leu Thr Pro His Pro Pro Gln Lys
        275                 280                 285

Gln Ala Tyr Gly Val Thr Leu Pro Thr Ser Val Leu Phe Ile Ala Gly
    290                 295                 300

His Asp Thr Asn Leu Ala Asn Leu Gly Gly Ala Leu Glu Leu Asn Trp
305                 310                 315                 320

Thr Leu Pro Gly Gln Pro Asp Asn Thr Pro Pro Gly Gly Glu Leu Val
                325                 330                 335

Phe Glu Arg Trp Arg Arg Leu Ser Asp Asn Ser Gln Trp Ile Gln Val
            340                 345                 350

Ser Leu Val Phe Gln Thr Leu Gln Gln Met Arg Asp Lys Thr Pro Leu
        355                 360                 365

Ser Leu Asn Thr Pro Pro Gly Glu Val Lys Leu Thr Leu Ala Gly Cys
    370                 375                 380

Glu Glu Arg Asn Ala Gln Gly Met Cys Ser Leu Ala Gly Phe Thr Gln
385                 390                 395                 400

Ile Val Asn Glu Ala Arg Ile Pro Ala Cys Ser Leu
```

-continued

<210> SEQ ID NO 2
<211> LENGTH: 60
<212> TYPE: DNA
<213> ORGANISM: Artificial Sequence
<220> FEATURE:
<223> OTHER INFORMATION: Forward Primer

<400> SEQUENCE: 2 gaagggtat ctctcgagaa aagagaggct caatctgaac cagaattgaa gttggaatct    60

<210> SEQ ID NO 3
<211> LENGTH: 42
<212> TYPE: DNA
<213> ORGANISM: Artificial Sequence
<220> FEATURE:
<223> OTHER INFORMATION: Reverse Primer

<400> SEQUENCE: 3
attattcgcg gccgcctatt acaaggaaca ggctgggatt ct    42

<210> SEQ ID NO 4
<211> LENGTH: 1281
<212> TYPE: DNA
<213> ORGANISM: Artificial Sequence
<220> FEATURE:
<223> OTHER INFORMATION: Nov9X gene

<400> SEQUENCE: 4 gaagggtat ctctcgagaa aagagaggct caatctgaac cagaattgaa gttggaatct    60
gttgtcattg tctccagaca cggtgttaga gctccaacta aggctactca gttgatgcaa   120
gatgttactc cagatgcttg gcctacctgg cctgttaagt tgggtgaatt gactccaaga   180
ggtggtgaat tgattgctta cttgggtcac tactggagac aaagattggt tgctgatggt   240
ttgttgccaa agtgtggttg tccacaatct ggtcaagttg ctatcattgc tgatgttgat   300
gaaagaacta gaaagactgg tgaagccttc gctgccggtt tggccccaga ctgtgctatc   360
actgttcaca ctcaagctga tacttcctct ccagatccat tgttcaaccc attgaagact   420
ggtgtctgtc aattggataa cgctaacgtt actgatgcca tcttggaaag agctggtggt   480
tctatcgctg acttcactgg tcactaccaa actgccttca gagaattgga aagagtcttg   540
aacttcccac aatctaactt gtgtttgaag agagagaagc aagacgaatc ttgttccttg   600
actcaagcct tgccatctga attgaaggtc tctgctgatt gtgtctcctt gactggtgct   660
gtctccttgg cttctatgtt gactgaaatc ttcttgttgc aacaagctca aggtatgcca   720
gaaccaggtt ggggtagaat cactgattct caccaatgga cacccttgtt gtccttgcac   780
aacgctcaat cgatttgct gcagagaact ccagaagtcg ctagatccag agctactcca   840
ttgttggact tgatcaagac cgctttgact ccacacccac acagaagca agcttacggt   900
gttaccttgc aacttctgt cttgttcatt gccggtcacg atactaactt ggctaacttg   960
ggtggtgcct tggaattgaa ctggaccttg ccaggtcaac cagataacac tccaccaggt  1020
ggtgaattgg tcttcgaaag atggcgtcga ctgtctgata actctcaatg gattcaagtc  1080
tccttggtct tccaaaacctt gcaacaaatg agagacaaga ctccattgtc cttgaacact  1140

```
ccaccaggtg aagtcaagtt gaccttggct ggttgtgaag aaagaaacgc tcaaggtatg    1200
tgttctttgg ctggtttcac tcaaatcgtc aacgaagcca gaatcccagc ctgttccttg    1260
taataggcgg ccgcgaataa t                                               1281
```